United States Patent
Lim et al.

(10) Patent No.: US 9,585,650 B2
(45) Date of Patent: Mar. 7, 2017

(54) SURGICAL SPACER INSTRUMENT AND METHOD

(71) Applicant: Warsaw Orthopedic, Inc., Warsaw, IN (US)

(72) Inventors: Roy Lim, Germantown, TN (US); Matthew M. Morrison, Cordova, TN (US); Kevin T. Foley, Germantown, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 366 days.

(21) Appl. No.: 14/290,518

(22) Filed: May 29, 2014

(65) Prior Publication Data

US 2015/0342586 A1    Dec. 3, 2015

(51) Int. Cl.
*A61B 17/02* (2006.01)
*A61B 17/00* (2006.01)

(52) U.S. Cl.
CPC .. *A61B 17/025* (2013.01); *A61B 2017/00738* (2013.01); *A61B 2017/0256* (2013.01)

(58) Field of Classification Search
CPC ... A61B 17/025; A61B 17/88; A61B 17/8852; A61B 17/885
See application file for complete search history.

(56) References Cited

U.S. PATENT DOCUMENTS

| | | |
|---|---|---|
| 5,171,278 A | 12/1992 | Pisharodi |
| 5,235,966 A | 8/1993 | Jamner |
| 5,390,683 A | 2/1995 | Pisharodi |
| 5,658,335 A | 8/1997 | Allen |
| 5,665,122 A | 9/1997 | Kambin |
| 5,782,832 A | 7/1998 | Larsen et al. |
| 5,888,224 A | 3/1999 | Beckers et al. |
| 6,039,761 A | 3/2000 | Li et al. |
| 6,045,579 A | 4/2000 | Hochshuler et al. |
| 6,080,193 A | 6/2000 | Hochshuler et al. |
| 6,102,950 A | 8/2000 | Vaccaro |
| 6,126,689 A | 10/2000 | Brett |
| 6,174,334 B1 | 1/2001 | Suddaby |
| 6,176,882 B1 | 1/2001 | Biedermann et al. |
| 6,179,873 B1 | 1/2001 | Zientek |
| 6,183,517 B1 | 2/2001 | Suddaby |
| 6,190,414 B1 | 2/2001 | Young et al. |
| 6,193,757 B1 | 2/2001 | Foley et al. |
| 6,217,579 B1 | 4/2001 | Koros |
| 6,332,895 B1 | 12/2001 | Suddaby |
| 6,582,451 B1 | 6/2003 | Marucci et al. |

(Continued)

FOREIGN PATENT DOCUMENTS

| | | |
|---|---|---|
| DE | 20004812 U1 | 9/2000 |
| EP | 0676176 | 10/1995 |

(Continued)

*Primary Examiner* — Andrew Yang

(57) ABSTRACT

A surgical instrument comprises a first member defining a longitudinal axis. A second member is connected with a pivot. A third member defines a first axis disposed at an angular orientation relative to the longitudinal axis and is connected with the pivot. The second member is translatable relative to the first member to rotate the pivot to move the third member between a first orientation and a second orientation to space vertebral tissue. Systems and methods are disclosed.

20 Claims, 25 Drawing Sheets

(56) References Cited

U.S. PATENT DOCUMENTS

| | | | |
|---|---|---|---|
| 7,070,598 B2 | 7/2006 | Lim et al. | |
| 7,087,055 B2 | 8/2006 | Lim | |
| 7,763,028 B2 | 7/2010 | Lim et al. | |
| 7,988,695 B2 * | 8/2011 | Dye | A61F 2/4611 606/86 A |
| 8,025,665 B2 | 9/2011 | Lim et al. | |
| 8,377,071 B2 | 2/2013 | Lim et al. | |
| 8,579,907 B2 | 11/2013 | Lim et al. | |
| 2003/0208203 A1 * | 11/2003 | Lim | A61B 17/7083 606/86 A |
| 2004/0153065 A1 * | 8/2004 | Lim | A61F 2/442 606/53 |
| 2006/0241643 A1 | 10/2006 | Lim et al. | |

FOREIGN PATENT DOCUMENTS

| | | |
|---|---|---|
| WO | 9525485 | 9/1995 |
| WO | 0141652 | 6/2001 |

\* cited by examiner

SURGICAL SPACER INSTRUMENT AND METHOD

TECHNICAL FIELD

The present disclosure generally relates to medical devices for the treatment of spinal disorders, and more particularly to a surgical system and method for treatment of a spine disorder.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes discectomy, laminectomy, fusion and implantable prosthetics. As part of these surgical treatments, implants, such as, for example, spinal constructs and interbody devices are often employed for stabilization of a treated section of a spine. For example, during surgical treatment, surgical instruments can be used to prepare a surgical site and the implants can be delivered to the surgical site for treating the spine section. This disclosure describes an improvement over these prior art technologies.

SUMMARY

In one embodiment, a surgical instrument is provided. The surgical instrument comprises a first member defining a longitudinal axis. A second member is connected with a pivot. A third member defines a first axis disposed at an angular orientation relative to the longitudinal axis and is connected with the pivot. The second member is translatable relative to the first member to rotate the pivot to move the third member between a first orientation and a second orientation to space vertebral tissue. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
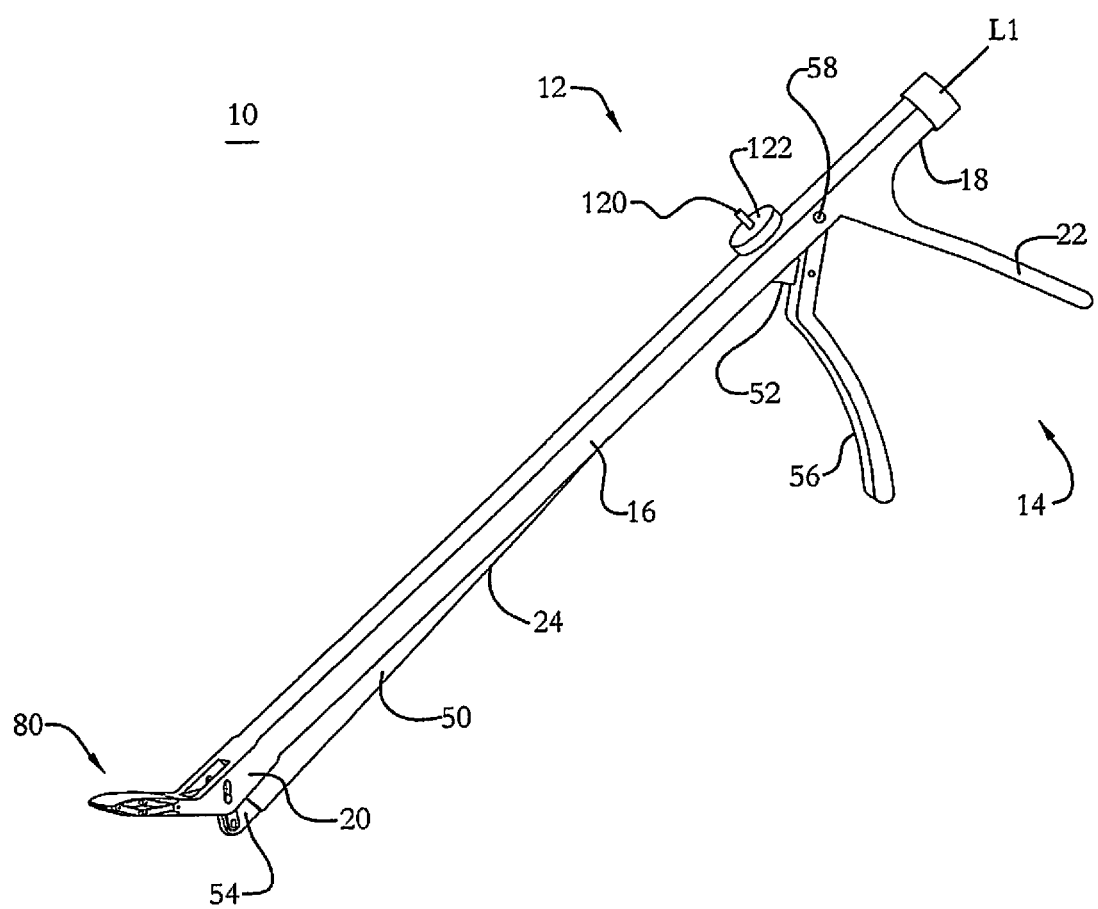
FIG. 1 is a perspective view of components of one embodiment of a surgical system in accordance with the principles of the present disclosure.

The exemplary embodiments of the system and related methods of use disclosed are discussed in terms of medical devices for the treatment of musculoskeletal disorders and more particularly, in terms of a surgical implant system and method for treatment of a spine disorder.

In one embodiment, the present system includes a surgical instrument that comprises an angled scissor jack distractor. In some embodiments, the surgical instrument includes an angled scissor jack distractor having an angular bell crank actuator that allows the device to be operated from an angle. In some embodiments, the surgical instrument can be employed with an oblique lateral interbody fusion (OLIF) procedure and/or avoids an iliac crest in lateral procedures in the lower lumbar spine. In some embodiments, the surgical instrument includes a sliding pivot bell-crank that allows a tip of the instrument to be off axis to a shaft of the instrument and allows the instrument to distract tissue in applications where there are anatomical constraints. In some embodiments, the surgical instrument comprises an angled anterior distractor that can be employed with procedures for treating a L5-S1 disorder, such as, for example, slip of vertebral bodies. In some embodiments, the surgical instrument can be employed with a procedure such that the surgical instrument is angled laterally to gain access to a disc space laterally and avoid the pelvis. In some embodiments, the surgical instrument can be employed with a procedure such that the surgical instrument is angled for use with an OLIF procedure.

In one embodiment, the present system includes a surgical instrument configured for an anterior approach with direct access to a disc space avoiding certain anatomical structures. In one embodiment, the instrument includes an angled portion configured to maneuver around obstacles. In one embodiment, the instrument includes an angled scissor jack. In one embodiment, the instrument includes a sliding pivot bell crank. In one embodiment, the present system includes a surgical instrument including a bell crank configured to actuate a scissor jack by axial translation of a shaft to vertically deploy plates of a tip of the instrument. In one embodiment, the axial force is not coaxial with the shaft of the tip.

In one embodiment, the present system includes a surgical instrument utilizing a lever style actuator. In one embodiment, the present system includes a surgical instrument having a threaded engagement actuator. In one embodiment, this configuration of the instrument can be employed with a surgical procedure including an anterior distraction of slipped vertebral bodies, for example, spondylolisthesis.

In one embodiment, the present system includes a surgical instrument configured to access an L5 vertebral body without removing a section of the vertebra thereby preserving more of the L5 vertebra resulting in greater stabilization. In one embodiment, the system includes an instrument having a width of 27 millimeters (mm), a length of 32 mm and a height of 7 mm in an un-deployed orientation.

In one embodiment, the present system includes a surgical instrument configured to be impacted with vertebral tissue to gain access into a disc space. In one embodiment, the instrument includes a lever that is actuated to deploy a tip. In one embodiment, the instrument utilizes a variable lordotic tip having unequal length links to adapt to increasing lordosis with increased distraction height. In some embodiments, the instrument includes parallel and/or lordotic adjustable tips. In one embodiment, the instrument is configured to allow for an angle change during axial translation of a scissor jack shaft.

In one embodiment, the present system includes a surgical instrument configured to allow for an angle change in an axial plane. In one embodiment, the instrument can be utilized with OLIF procedures. In one embodiment, the present system includes a surgical instrument utilizing a lever style actuator. In one embodiment, the present system includes a surgical instrument having a threaded engagement actuator to deploy a scissor jack tip. In one embodiment, the present system includes a surgical instrument having a laterally angled scissor jack tip, a sagittal angled scissor jack tip and/or a combination of bother lateral and sagittal angles.

In some embodiments, one or all of the components of the system may be disposable, peel pack and/or pre packed sterile devices. One or all of the components of the system may be reusable. The system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic and pelvic regions of a spinal column. The system and methods of the present disclosure may also be used on animals, bone modus and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, vessels, ligaments, tendons, cartilage and/or bone unless specifically referred to otherwise.

The following discussion includes a description of a surgical system, related components and methods of employing the system in accordance with the principles of the present disclosure. Alternate embodiments are also disclosed. Reference is made in detail to the exemplary embodiments of the present disclosure, which are illustrated in the accompanying figures. Turning to FIGS. 1-6, there are illustrated components of a system, such as, for example, a surgical system 10 in accordance with the principles of the present disclosure.

The components of system 10 can be fabricated from biologically acceptable materials suitable for medical applications, including metals, synthetic polymers and/or ceramics. For example, the components of system 10, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, super-elastic metallic alloys (e.g., Nitinol, super elastoplastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, partially resorbable materials, such as, for example; composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

Figure 5:
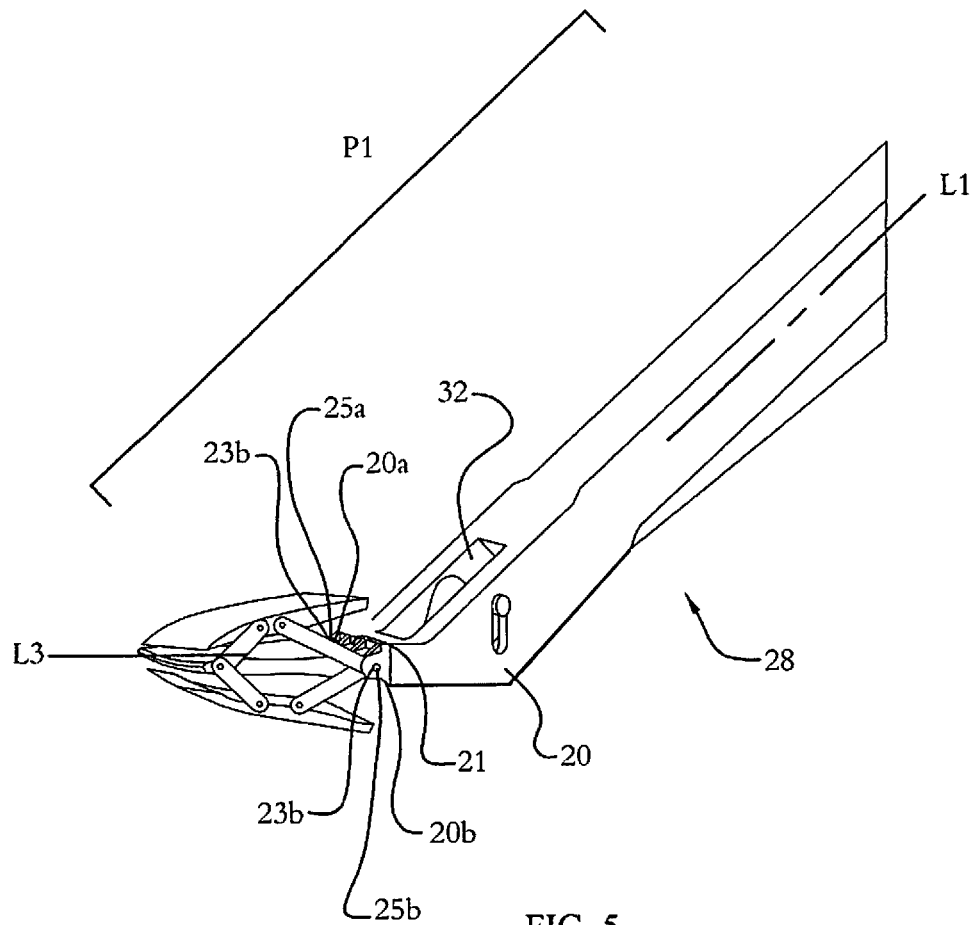
FIG. 5 is a perspective view of the components shown in FIG. 2.

System 10 includes an instrument 12 configured for engagement with tissue, such as, for example, vertebrae, as described herein. Instrument 12 includes a member, such as, for example, a handle 14. Handle 14 includes a shaft 16 extending between an end 18 and an end 20. Shaft 16 defines a longitudinal axis L1 extending in a plane P1, as shown in FIG. 5, of instrument 12. In some embodiments, shaft 16 may have alternate cross section shapes, such as, for example oval, oblong, triangular, square, polygonal, irregular, uniform, non-uniform, offset, staggered, undulating, arcuate, variable and/or tapered.

End 18 includes an actuator, such as, for example, a lever 22. Lever 22 is fixed with shaft 16. In one embodiment, lever 22 is connected with shaft 16 via a hinge (not shown). In some embodiments, the cross section and/or overall configuration of lever 22 may be variously configured, such as, for example, round, oval, oblong, square, rectangular, polygonal, irregular, uniform, non-uniform, offset, staggered, tapered, consistent or variable. Lever 22 is configured for engagement with a lever of a second member, such as, for example, an actuator 24, as discussed herein.

Figure 3:
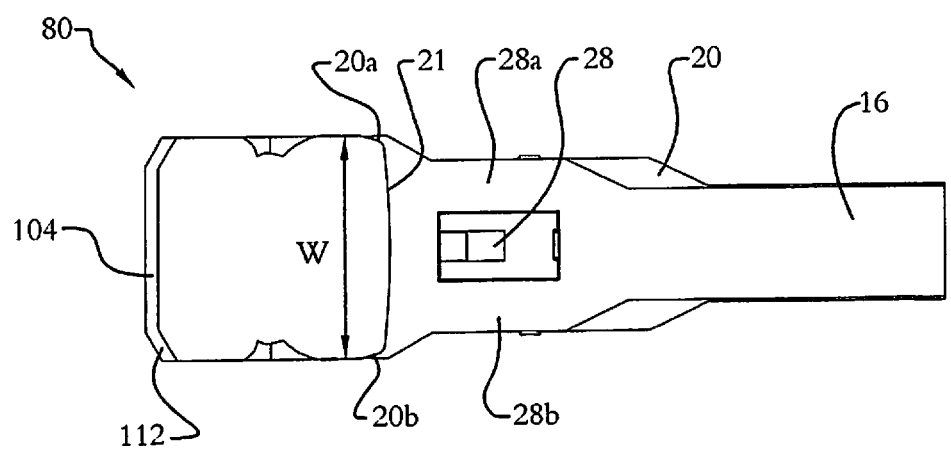
FIG. 3 is a side view of the components shown in FIG. 2.

End 20 includes extensions 20a and 20b, as shown in FIG. 3. Extensions 20a, 20b define a cavity 21. Cavity 21 is configured to receive a width w of a member, such as, for example a vertebral spacer 80. Extensions 20a, 20b are configured for connection with spacer 80, as discussed herein. Extension 20a includes an inner surface 23a that defines an opening 25a configured to receive a pin of spacer 80, as discussed herein and as shown in FIG. 5. Extension 20b includes an inner surface 23b that defines an opening 25b configured to receive a pin of spacer 80, as discussed herein.

Figure 4:
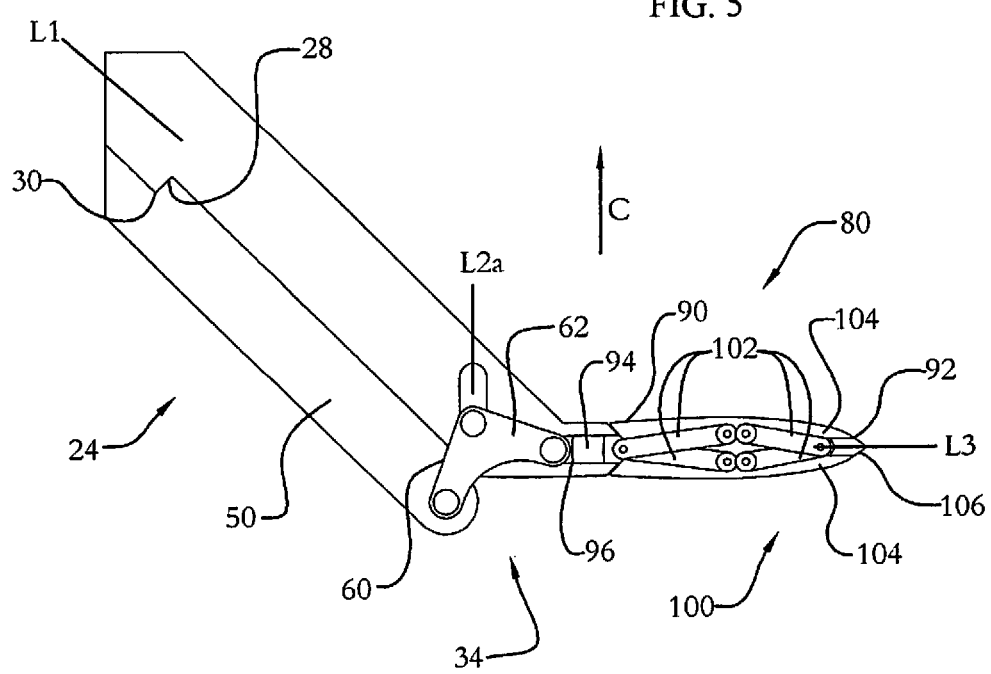
FIG. 4 is a cross section view of the components shown in FIG. 2.

Shaft 16 includes a surface 26 that defines a cavity 28. Cavity 28 extends along axis L1. Cavity 28 includes an elongate portion 30 configured for movable disposal of actuator 24, as discussed herein. Cavity 28 includes an end portion 32 disposed at end 20 configured for disposal of a pivot, such as, for example, a bell crank 34, as discussed herein and as shown in FIG. 4. In some embodiments, cavity 28 may have alternate cross section shapes, such as, for example oval, oblong, triangular, square, polygonal, irregular, uniform, non-uniform, offset, staggered, undulating, arcuate, variable and/or tapered. In some embodiments, surface 26 may be, such as, for example, rough, arcuate, undulating, mesh, porous, semi-porous, dimpled and/or textured.

Figure 2:
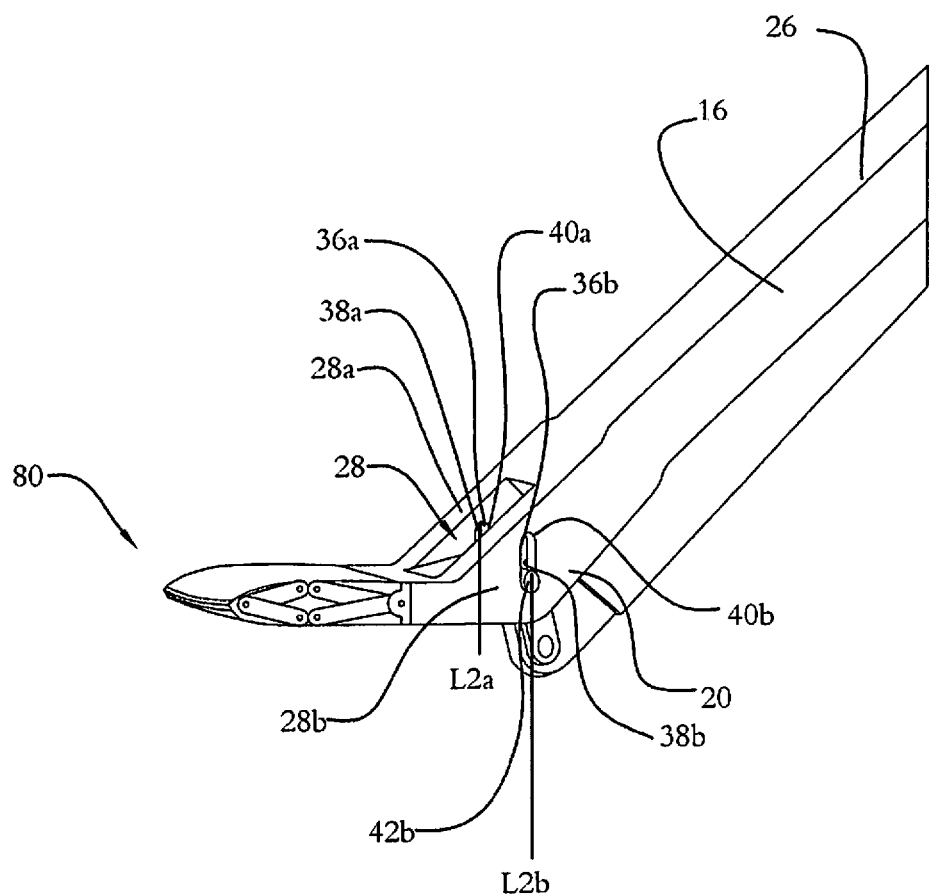
FIG. 2 is a break away perspective view of the components of the system shown in FIG. 1.

Surface 26 includes arms 28a and 28b, as shown in FIG. 2, configured for engagement with bell crank 34, as described herein. Arm 28a includes an inner surface 36a that defines a cavity, such as, for example, an elongated transverse slot 38a, as shown in FIG. 4. Slot 38a defines a longitudinal axis L2a and includes an end 40a and an end 42a. Axis L2a is disposed transverse to axis L1. Slot 38a is configured for moveable disposal of bell crank 34 such that bell crank 34 translates along slot 38a between end 40a and end 42a.

Arm 28b includes an inner surface 36b that defines a cavity, such as, for example, an elongated slot 38b, as shown in FIG. 2. Slot 38b defines a longitudinal axis L2b and includes an end 40b and an end 42b. Axis L2b is disposed transverse to axis L1 and parallel to axis L2a. Slot 38b is configured for moveable disposal of bell crank 34 such that bell crank 34 translates along slot 38b between end 40b and end 42b.

Actuator 24 includes a shaft 50, as shown in FIG. 1. Shaft 50 includes an end 52 and an end 54 and extends along axis L1. End 52 includes a lever 56 configured for movement relative to lever 22 for translating bell crank 34 and/or actuating spacer 80. Lever 56 is connected with shaft 50 via a hinge 58. Hinge 58 is configured to facilitate rotation of lever 56 relative to axis L1 to translate shaft 50. In some embodiments, the cross section and/or overall configuration of lever 56 may be variously configured, such as, for example, round, oval, oblong, square, rectangular, polygonal, irregular, uniform, non-uniform, offset, staggered, tapered, consistent or variable. Relative movement of lever 22 and lever 56 causes shaft 50 to translate in cavity 28 relative to shaft 16. Lever 56 includes an outer surface that may be, such as, for example, rough, arcuate, undulating, mesh, porous, semi-porous, dimpled and/or textured to facilitate gripping.

Figure 6:
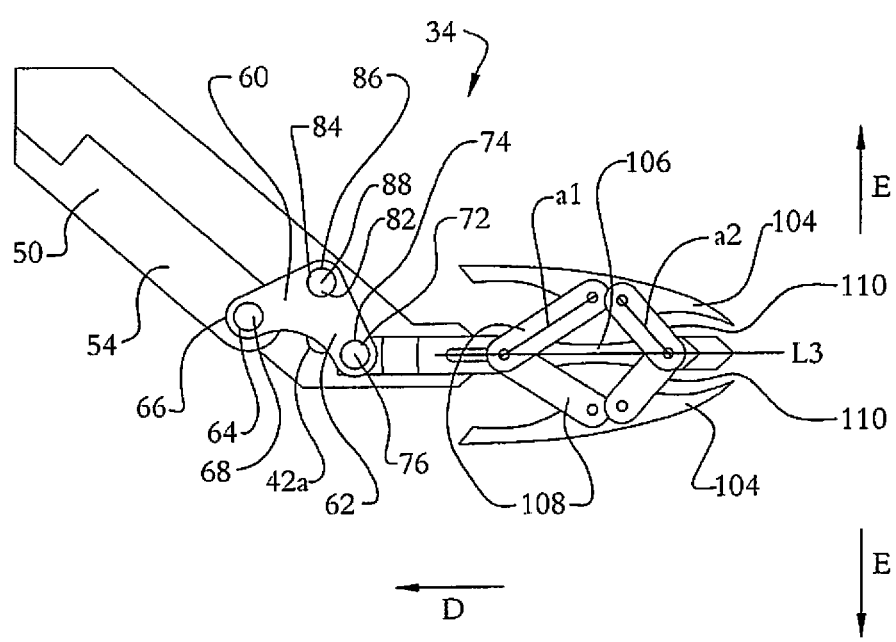
FIG. 6 is a cross section view of the components shown in FIG. 2.

End 54 includes bell crank 34. Bell crank 34 includes a part 60 and a part 62 disposed in substantially perpendicular orientation. Part 60 includes an inner surface 64 that defines an opening 66, as shown in FIG. 6. Opening 66 is configured to receive a hinge, such as for example, a pin 68. Part 60 is configured for connection with shaft 50 via pin 68 disposed within an opening of shaft 50. Part 62 includes an inner surface 72 that defines an opening 74. Opening 74 is configured to receive a hinge, such as for example, a pin 76. Part 62 is configured for connection with spacer 80 via pin 76.

Part 60 and part 62 are disposed in a perpendicular configuration and define a pivot 82. In some embodiments, part 60 may extend transverse and/or at other angular orientations such as acute or obtuse, co-axial and/or may be offset or staggered with respect to part 62. Pivot 82 includes an inner surface 84 that defines an opening 86 configured to receive an element, such as, for example, a pin 88. Pin 88 is configured for disposal in slots 38a, 38b. Translation of pin 88 along slots 38a, 38b causes parts 60, 62 to rotate to move spacer 80 between a first orientation and a second orientation, as described herein.

Spacer 80, as shown in FIGS. 4-6, defines a longitudinal axis L3 and includes an end 90 and an end 92. Axis L3 is disposed at an angular orientation relative to axis L1. In some embodiments, axis L3 is disposed at an angle relative to axis L1 in a range of approximately 10-160 degrees. In some embodiments, axis L3 may extend transverse and/or at other angular orientations such as acute or obtuse, co-axial and/or may be offset or staggered relative to axis L1. End 90 includes a shaft 94. Shaft 94 includes an opening 96 configured for connection with pin 76 of part 62.

Spacer 80 includes a linkage 100 that may include a number of linkages 102 positioned between plates 104. Each individual linkage 102 mates with a complimentary linkage 102 disposed with a pull arm 106 to provide movement to spacer 80. As shown in FIG. 6, spacer 80 includes two pairs of linkages 108 and another two pairs of linkages 110 for a total of four pairs of linkages, or eight total linkages. Linkages 108 include a length a1 and linkages 110 include a length a2. In one embodiment, length a1 is longer than length a2. In one embodiment, length a1 is shorter than length a2. A non-equal length a1 and length a2 configuration facilitates adjustable spacing of vertebrae by spacer 80 to provide a variable lordotic spacer. Each linkage 102 may have a variety of shapes and configurations. Linkages 108, 110 are configured for connection with extensions 20a, 20b via pins such that linkages 108, 110 are configured to rotate relative to extensions 20a, 20b.

Plates 104 are positioned on a first side and a second side of spacer 80 to contact vertebral members, such as, for example, endplates of vertebrae. Plates 104 each include a contact surface having a surface area to distribute the disc space load created by spacer 80 across a region of the vertebral members. As shown in FIG. 6, the different lengths of linkages 108, 110 causes the contact surfaces to expand at an angular orientation relative to axis L3 to accommodate varying lordosis of vertebrae. In some embodiments, plates 104 are configured for expansion in plane P1 of instrument 12.

Spacer 80 is adjustable between a first, collapsed orientation, as shown in FIG. 4, and a second, expanded orientation, as shown in FIGS. 5 and 6. In the collapsed orientation, spacer 80 has a reduced size to facilitate introduction, insertion and delivery with a patient and/or a surgical pathway to a surgical site, and between vertebral members. In the expanded orientation, spacer 80 has an enlarged size for contacting, spacing apart and spreading the vertebral members. In some embodiments, shaft 94 operatively connects bell crank 34 to linkages 108, 110 to adjust spacer 80 to positions between a first orientation and a second orientation.

Instrument 12 includes a lock to maintain instrument 12 in a fixed position in the expanded orientation. In one embodiment, as shown in FIG. 1, lever 56 includes a lock surface such as, for example, a threaded portion 120 configured for engagement with a threaded nut 122 to fix spacer 80 and lever 56 in a selected orientation.

Figure 7:
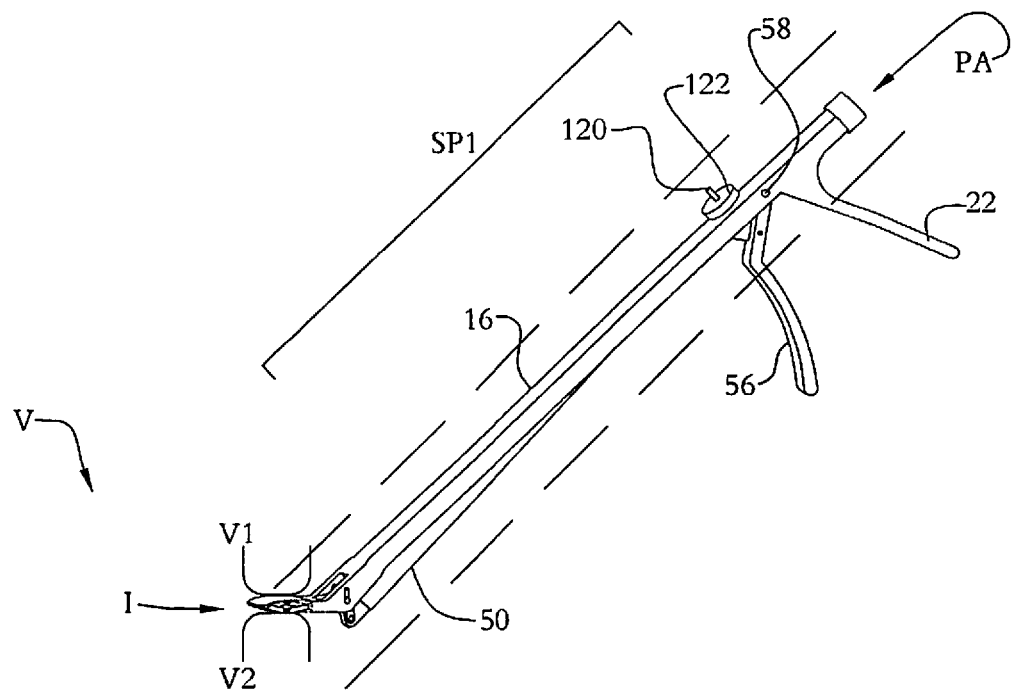
FIG. 7 is a perspective view of components of one embodiment of a surgical system in accordance with the principles of the present disclosure disposed with vertebrae.

In operation, instrument 12 is manipulated to insert spacer 80 between vertebrae such that spacer 80 is disposed in a collapsed orientation, as shown in FIG. 7, to facilitate introduction, insertion and delivery of spacer 80 along a surgical pathway and/or at a surgical site. In the collapsed orientation, spacer 80 is disposed between vertebrae, engaging vertebral tissue and/or having one or both of plates 104 contacting vertebrae. Upon selective disposal of spacer 80 with vertebrae, levers 22, 56 are disposed in a non-compressed orientation, as shown in FIG. 7. Lever 56 is manipulated such that lever 56 rotates about hinge 58, in the directions shown by arrow A.

Figure 8:
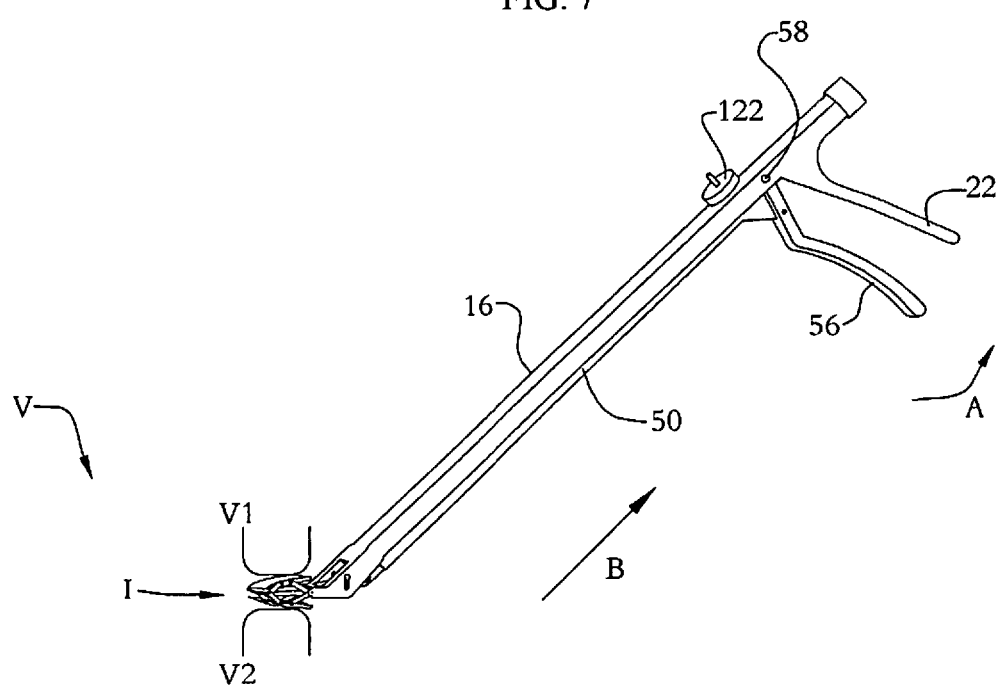
FIG. 8 is a perspective view of components and vertebrae shown in FIG. 7.
Figure 9:
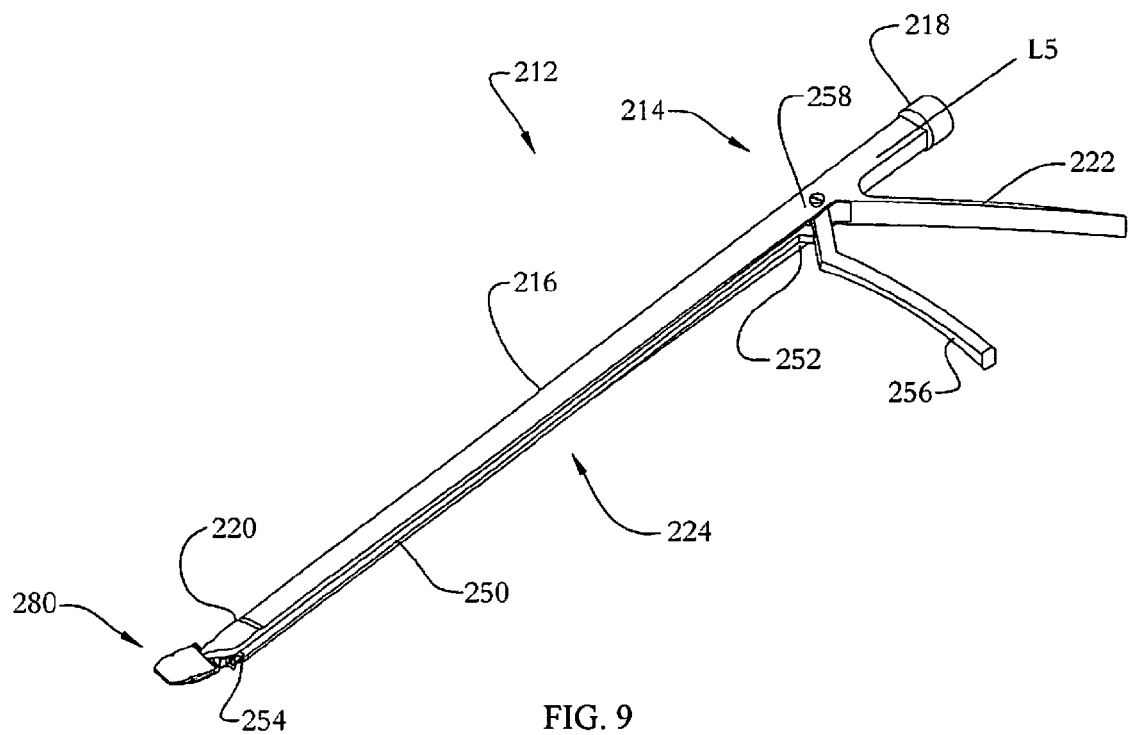
FIG. 9 is a perspective view of components of one embodiment of a surgical system in accordance with the principles of the present disclosure.

Compression of lever 56 causes shaft 50 to translate along portion 30, in the direction shown by arrow B in FIG. 8, relative to shaft 16. Translation of shaft 50 causes bell crank 34 to pivot about pin 68 relative to shaft 50. Pin 88 translates along slots 38a, 38b from ends 42a, 42b to ends 40a, 40b, in the direction shown by arrow C in FIG. 4. Translation of pin 88 causes portion 62 to pivot about pin 76 to engage shaft 96 causing shaft 96 to translate, in the direction shown by arrow D in FIG. 6. Translation of shaft 96 causes pull arm 106 to actuate expansion of spacer 80. Linkages 108, 110 pivot about pull arm 106 and extensions 20a, 20b causing plates 104 to expand, in the direction shown by arrow E in FIG. 6. Expansion of plates 104 causes surfaces 112 to engage vertebral surfaces.

In assembly, operation and use, as shown in FIGS. 7 and 8, system 10, similar to the systems and methods described herein, is employed with a surgical procedure, such as, for example, a fusion treatment of a spine of a patient including vertebrae V, intervertebral disc space I and body areas adjacent thereto, as discussed herein. In some embodiments, one or all of the components of system 10 can be delivered or implanted as a pre-assembled device or can be assembled in situ. In some embodiments, one or all of the components of system 10 may be completely or partially revised, removed or replaced.

For example, system 10 can be employed with a surgical arthrodesis procedure, such as, for example, an interbody fusion for treatment of an applicable condition or injury of an affected section of a spinal column and adjacent areas within a body, such as, for example, intervertebral disc space I between a vertebra V1 and a vertebra V2 of vertebrae V. In some embodiments, system 10 can include an intervertebral implant that can be inserted with intervertebral disc space I to space apart articular joint surfaces, provide support and maximize stabilization of vertebrae V. In some embodiments, system 10 may be employed with one or a plurality of vertebra.

A medical practitioner obtains access to a surgical site including vertebrae V1, V2 such as through incision and retraction of tissues. System 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. In one embodiment, the components of system 10 are delivered through a surgical pathway PA to the surgical site along a surgical approach into intervertebral disc space I. In one embodiment, surgical instrument 12 is delivered along an anterior surgical approach with direct access to intervertebral disc space I such that selected anatomical structures can be avoided due to the angled orientation of spacer 80, as described herein. In some embodiments, the angled orientation of spacer 80 provides an anterior distractor that can be employed with procedures for treating a L5-S1 disorder, such as, for example, slip of vertebral bodies. In one embodiment, surgical instrument 12 can be employed with a surgical procedure for an anterior distraction of slipped vertebral bodies, for example, spondylolisthesis. Once access to the surgical site is obtained, the particular surgical procedure can be performed for treating the spine disorder.

A preparation instrument (not shown) can be employed to prepare tissue surfaces of vertebrae V, as well as for aspiration and irrigation of a surgical region. Instrument 12 is initially locked with nut 122 to maintain spacer 80 in a collapsed orientation. Instrument 12 is manipulated to insert spacer 80 with disc space I and between vertebrae V1, V2 such that spacer 80 is disposed in a collapsed orientation, as shown in FIG. 7. Instrument 12 is inserted for disposal within a sagittal plane SP1 of the body. Plate 104 is in contact with at least vertebra V2. Upon disposal of spacer 80 with vertebrae, levers 22, 56 are disposed in a non-compressed orientation, as shown in FIG. 7.

Lever 56 is compressed causing shaft 50 to translate along portion 30, in the direction shown by arrow B in FIG. 8. Translation of shaft 50 causes bell crank 34 to pivot about pin 68 relative to shaft 50. Pin 88 translates along slots 38a, 38b from ends 42a, 42b to ends 40a, 40b, in the direction shown by arrow C in FIG. 4. Translation of pin 88 causes portion 62 to pivot about pin 76 to engage shaft 96 causing shaft 96 to translate, in the direction shown by arrow D in FIG. 6. Translation of shaft 96 causes pull arm 106 to actuate expansion of spacer 80. Linkages 108, 110 pivot about pull arm 106 and extensions 20a, 20b causing plates 104 to expand, in the direction shown by arrow E in FIG. 6, along plane SP1. Expansion of plates 104 causes the contact surfaces to engage the surfaces of vertebrae V1, V2 Spacer 80 expands to an enlarged size for contacting, spacing apart and/or spreading vertebrae V1, V2.

In some embodiments, trial implants (not shown) are delivered along surgical pathway PA. In some embodiments, one or a plurality of interbody implants can be introduced and delivered along surgical pathway PA for implantation with vertebrae V1, V2. In some embodiments, pilot holes or the like are made in vertebrae V1, V2 adjacent intervertebral space I, via surgical pathway PA for receiving bone fasteners and/or attaching spinal constructs, which may include rods and plates.

The components of system 10 can be made of radiolucent materials such as polymers. Radiomarkers may be included for identification under x-ray, fluoroscopy, CT or other imaging techniques. In some embodiments, the use of microsurgical and image guided technologies may be employed to access, view and repair spinal deterioration or damage, with the aid of system 10. Upon completion of the procedure, the surgical instruments, assemblies and non-implant components of system 10 are removed from the surgical site and the incision is closed.

Figure 10:
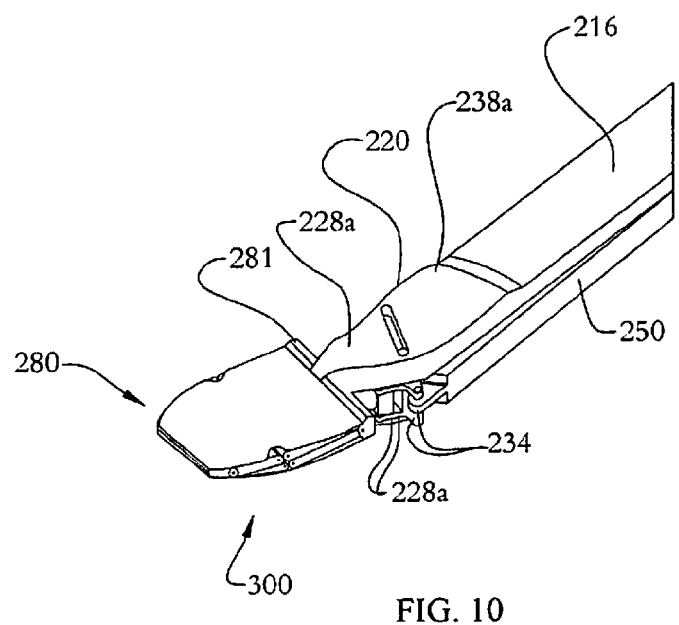
FIG. 10 is a break away view of the components shown in FIG. 9.
Figure 11:
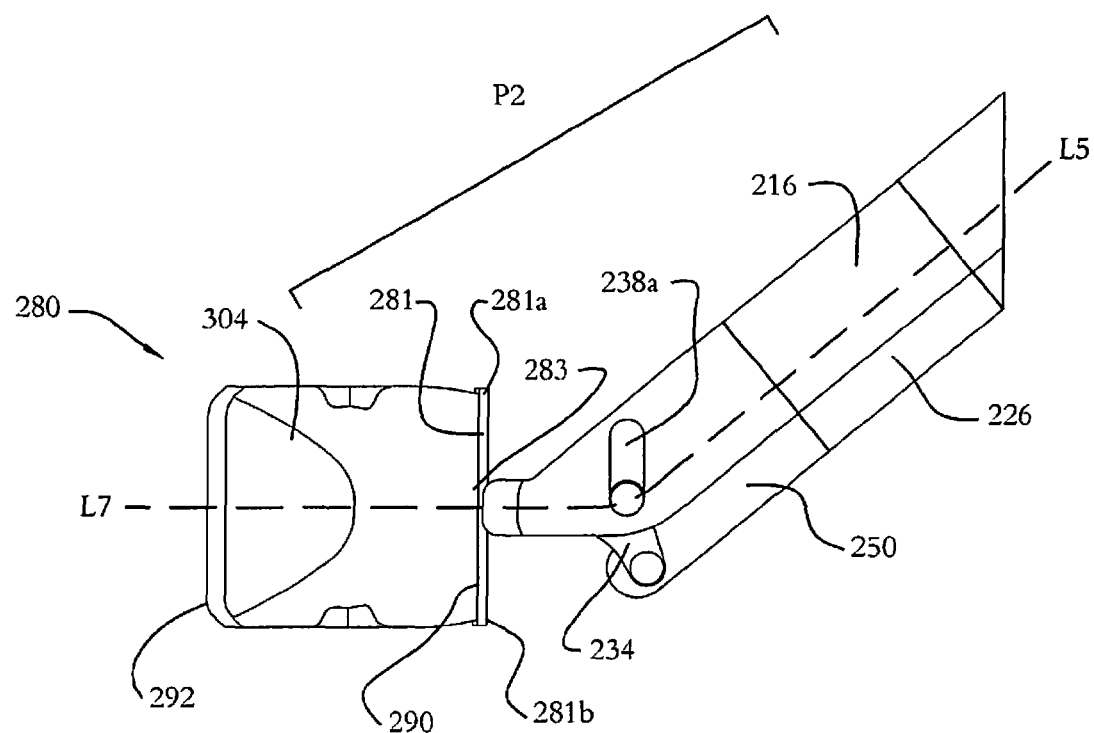
FIG. 11 is a break away view of the components shown in FIG. 9.

In one embodiment, as shown in FIGS. 9-13, system 10, similar to the systems and methods described with regard to FIGS. 1-8, comprises instrument 212, similar to instrument 12 described herein. Instrument 212 includes a handle 214. Handle 214 includes a shaft 216 extending between an end 218 and an end 220. Shaft 216 defines a longitudinal axis L5 extending in a plane P2 of instrument 212, as shown in FIG. 11.

Figure 12:
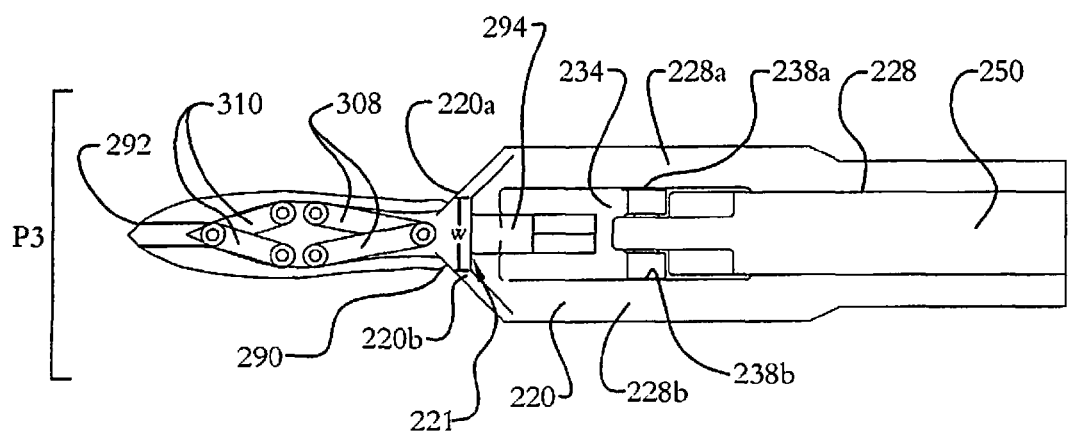
FIG. 12 is a side cross section view of the components shown in FIG. 11.

End 220 includes extensions 220a and 220b, as shown in FIG. 12. Extensions 220a, 220b define a cavity 221. Cavity 221 is configured to receive a width w1 of a linkage bar 281 of a vertebral spacer 280, similar to spacer 80 described herein. Extensions 220a, 220b are configured for connection with spacer 280, as discussed herein.

End 218 includes a lever 222. Lever 222 is fixed with shaft 216. Lever 222 is configured for engagement with a lever of an actuator 224, as discussed herein. Shaft 216 includes an outer surface 226 that defines a cavity 228. Surface 226 includes arms 228a, 228b that define slots 238a, 238b respectively, which are configured for engagement with bell crank 234, similar to bell crank 34 described herein.

Actuator 224 includes a shaft 250. Shaft 250 includes an end 252 and an end 254 and extends along axis L5. End 250 includes a lever 256 configured for movement relative to lever 222. Lever 256 is connected with shaft 250 via a hinge 258. Hinge 258 is configured to facilitate rotation of lever 256 relative to axis L5 to translate shaft 250.

End 254 includes bell crank 234, similar to bell crank 34, described herein. Bell crank 234 includes a part 260 and a part 262. Bell crank 234 includes a pin 288. Pin 288 is configured for disposal in slots 238a, 238b. Translation of pin 288 along slots 238a, 238b causes bell crank 234 to rotate to move spacer 280 between a first orientation and a second orientation, as described herein.

Spacer 280 includes an end 290 and an end 292 and defines a longitudinal axis L7. Axis L7 is disposed at an angular orientation relative to axis L5. In some embodiments, axis L7 is disposed at an angle relative to axis L5 in a range of approximately 10-160 degrees. In some embodiments, axis L7 may extend transverse and/or at other angular orientations such as acute or obtuse, co-axial and/or may be offset or staggered relative to axis L5. End 290 includes a shaft 294.

Spacer 280 includes a linkage 300 and linkage bar 281. As shown in FIG. 12, spacer 280 includes two pairs of linkages 308 and another two pairs of linkages 310 for a total of four pairs of linkages, or eight total linkages. Linkage bar 281 extends along end 290. Linkage bar 281 includes extensions 281a and 281b. Extensions 281a, 281b define a cavity 283. Cavity 283 is sized to receive a length of end 290. Extensions 281a, 281b are configured for connection with spacer 280. Extension 281b includes an inner surface 285 that defines an opening 287 configured to receive a pin, of linkage 310. Extension 281a, similar to extension 281b, includes an inner surface (not shown) that defines an opening (not shown) configured to receive a pin (not shown) of linkage 308.

Plates 304 are positioned on a first side and a second side of spacer 280 to contact vertebral members, such as, for example, endplates of vertebrae, as described herein. Plates 304 each include a contact surface having a surface area to distribute the disc space load created by spacer 280 across a region of the vertebral members. Plates 304 are configured for expansion in a plane P3 of instrument 212, as shown in FIG. 12. Plane P3 is disposed transverse to plane P2. In some embodiments, plane P2 is disposed substantially orthogonal to plane P3. In some embodiments, plane P3 comprises an axial plane of vertebrae such that spacer 280 is expandable in the axial plane.

Figure 13:
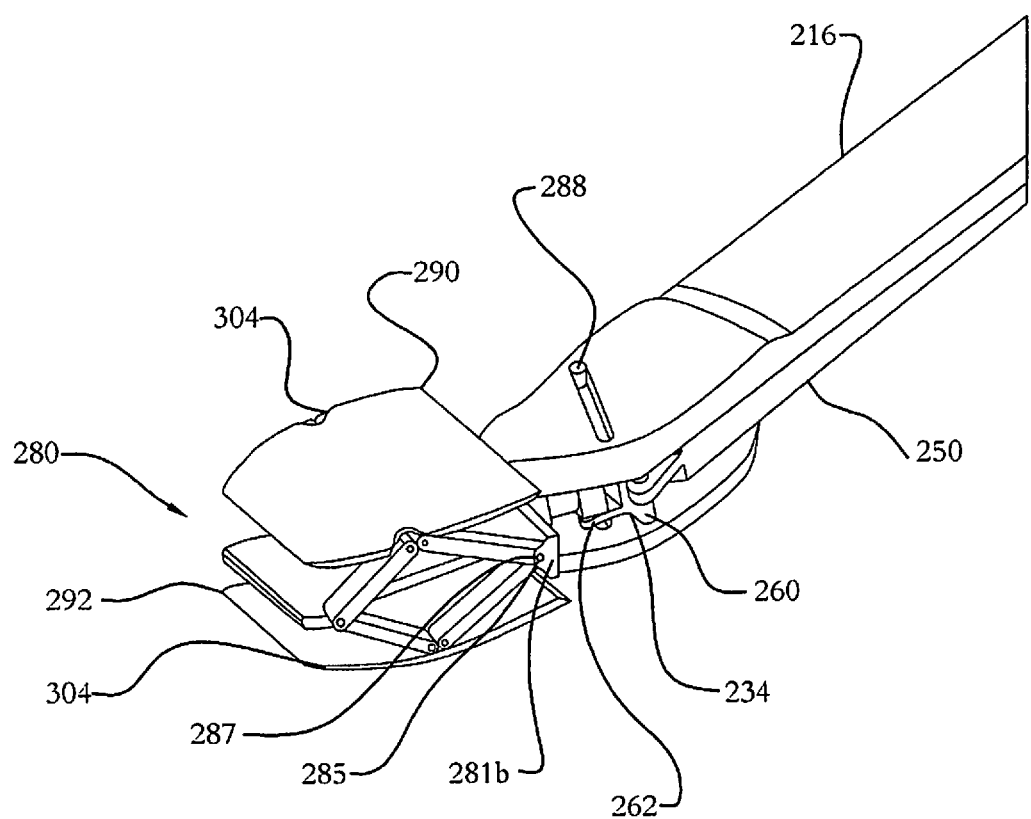
FIG. 13 is a perspective view of the components shown in FIG. 10.
Figure 14:
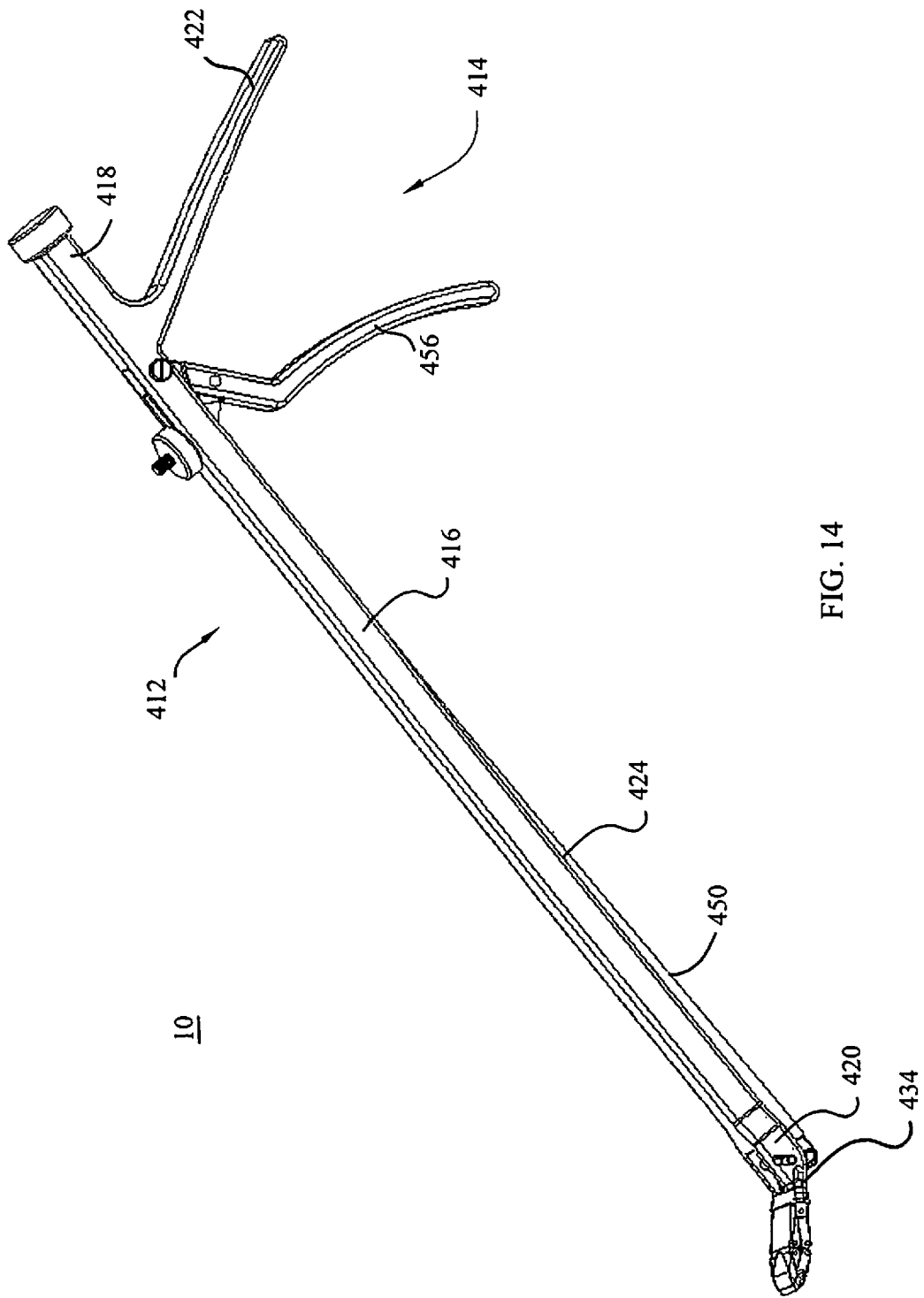
FIG. 14 is a perspective view of components of one embodiment of a surgical system in accordance with the principles of the present disclosure.

Spacer 280 is adjustable between a first orientation, as shown in FIG. 10, and a second orientation, as shown in FIG. 13, similar to the orientations described herein. In the first orientation, such as, for example, a collapsed orientation, spacer 280 has a reduced size to facilitate introduction, insertion and delivery with a patient and/or a surgical pathway to a surgical site, and between vertebral members. In the second orientation, such as, for example, an expanded orientation, spacer 280 has an enlarged size for contacting, spacing apart and spreading the vertebral members.

In assembly, operation and use, system 10 including surgical instrument 212, similar to the systems and methods described herein, is employed with a surgical procedure, such as, for example, a fusion treatment of a spine of a patient including vertebrae, an intervertebral disc space and body areas adjacent thereto, as discussed herein. In one embodiment, surgical instrument 212 is delivered through a surgical pathway to a surgical site along a surgical approach into an intervertebral disc space. In one embodiment, surgical instrument 212 is delivered along a lateral surgical approach with access to the intervertebral disc space such that selected anatomical structures can be avoided due to the angled orientation of spacer 280. In one embodiment, surgical instrument 212 is delivered along an OLIF surgical approach with access to the intervertebral disc space such that selected anatomical structures can be avoided due to the angled orientation of spacer 280. In some embodiments, surgical instrument 212 can be employed with a procedure such that surgical instrument 212 is angled laterally to gain access to a disc space laterally and avoid the pelvis. In some embodiments, surgical instrument 212 can be employed with an OLIF procedure to avoid an iliac crest in lateral procedures in the lower lumbar spine.

Figure 15:
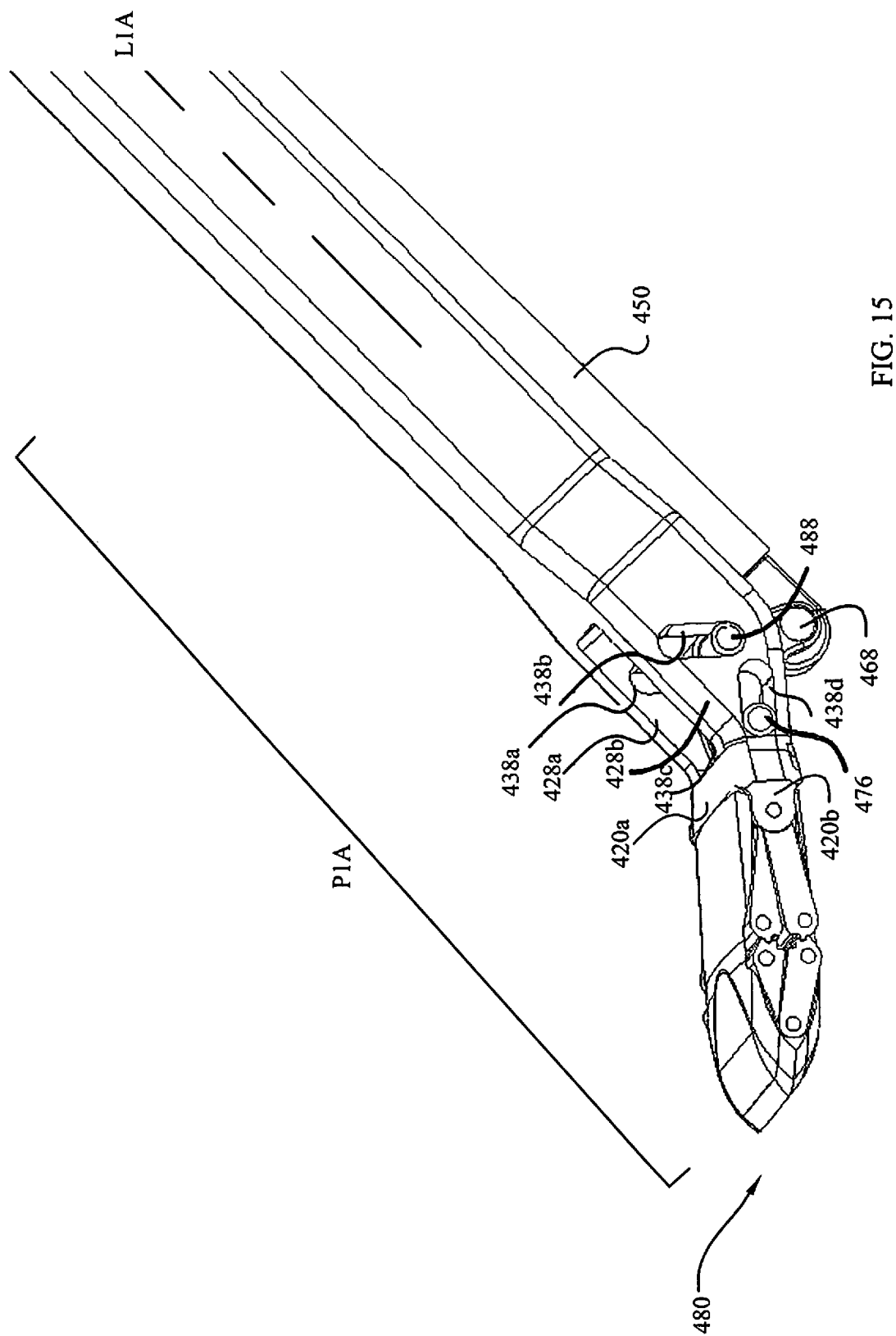
FIG. 15 is a break away perspective view of the components of the system shown in FIG. 14.

In one embodiment, as shown in FIGS. 14-18, system 10, similar to the systems and methods described with regard to FIGS. 1-8, comprises an instrument 412, similar to instrument 12 described herein. Instrument 412 includes a handle 414, similar to handle 14 described herein. Handle 414 includes a shaft 416 extending between an end 418 and an end 420. Shaft 416 defines a longitudinal axis L1A extending in a plane P1A, as shown in FIG. 15, of instrument 412.

End 418 includes an actuator, such as, for example, a lever 422, similar to lever 22 described herein. Lever 422 is configured for engagement with a lever of a second member, such as, for example, an actuator 424, similar to actuator 24, as described herein. End 420 includes extensions 420a and 420b that connect with a vertebral spacer 480, similar to spacer 80 described herein.

Figure 16:
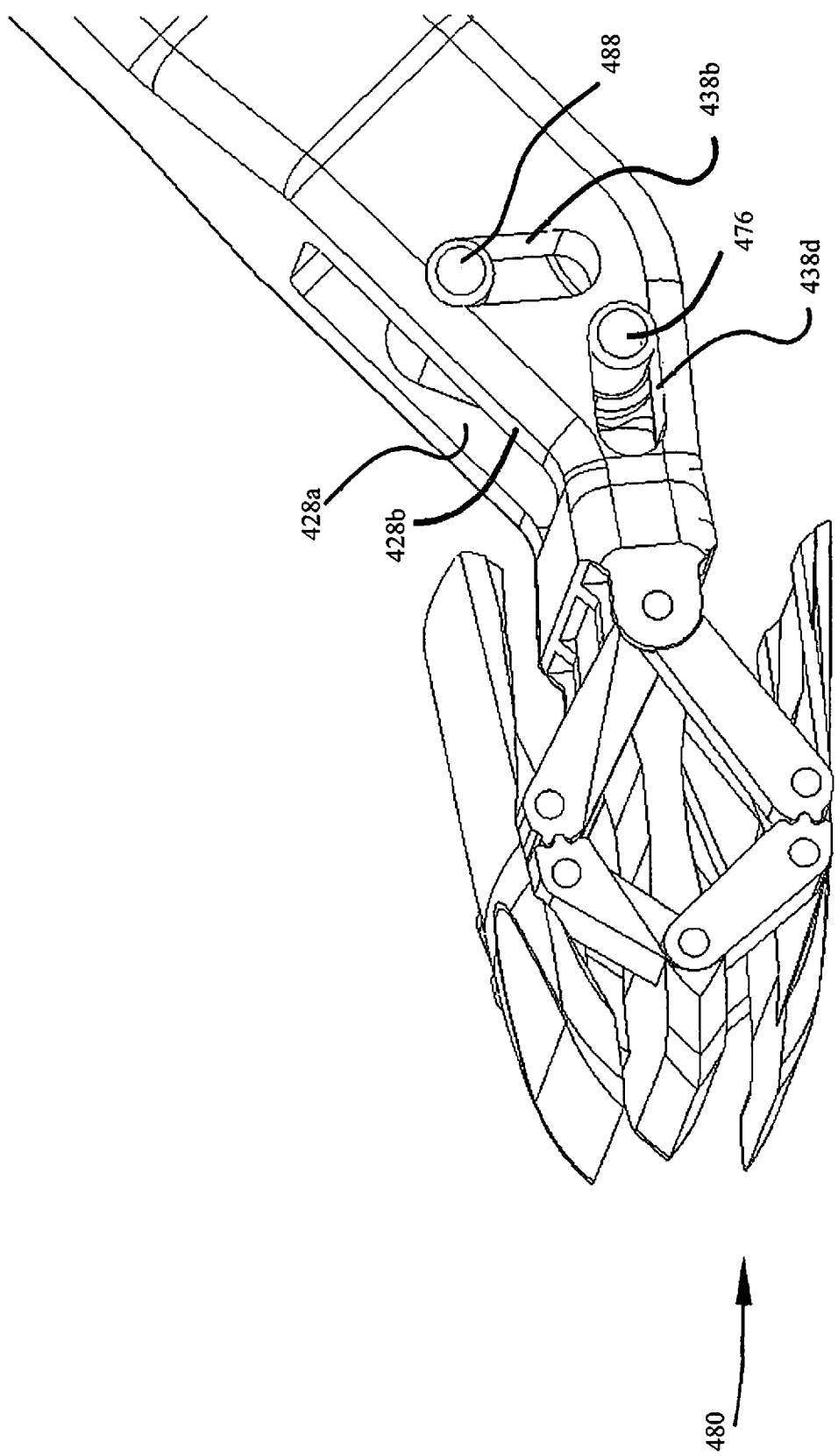
FIG. 16 is a perspective view of the components shown in FIG. 14.

End 420 includes arms 428a and 428b, as shown in FIGS. 15 and 16, configured for engagement with a bell crank 434, similar to bell crank 34 described herein. Arm 428a includes an inner surface that defines a transverse slot 438a, similar to slot 38a described herein. Slot 438a is configured for moveable disposal of a pin 488 of bell crank 434 such that bell crank 434 translates along slot 438a between ends thereof. Arm 428b includes an inner surface that defines a slot 438b, similar to slot 38b described herein. Slot 438b is configured for moveable disposal of pin 488 such that bell crank 434 translates along slot 438b between ends thereof.

The inner surface of arm 428a also defines a transverse slot 438c, similar to the slots 38 described herein. Slot 438c is configured for moveable disposal of a pin 476 of bell crank 434 such that bell crank 434 translates along slot 438c between ends thereof. The inner surface of arm 428b also defines a slot 438d, similar to the slots 38 described herein. Slot 438d is configured for moveable disposal of pin 476 such that bell crank 434 translates along slot 438d between ends thereof.

Figure 18:
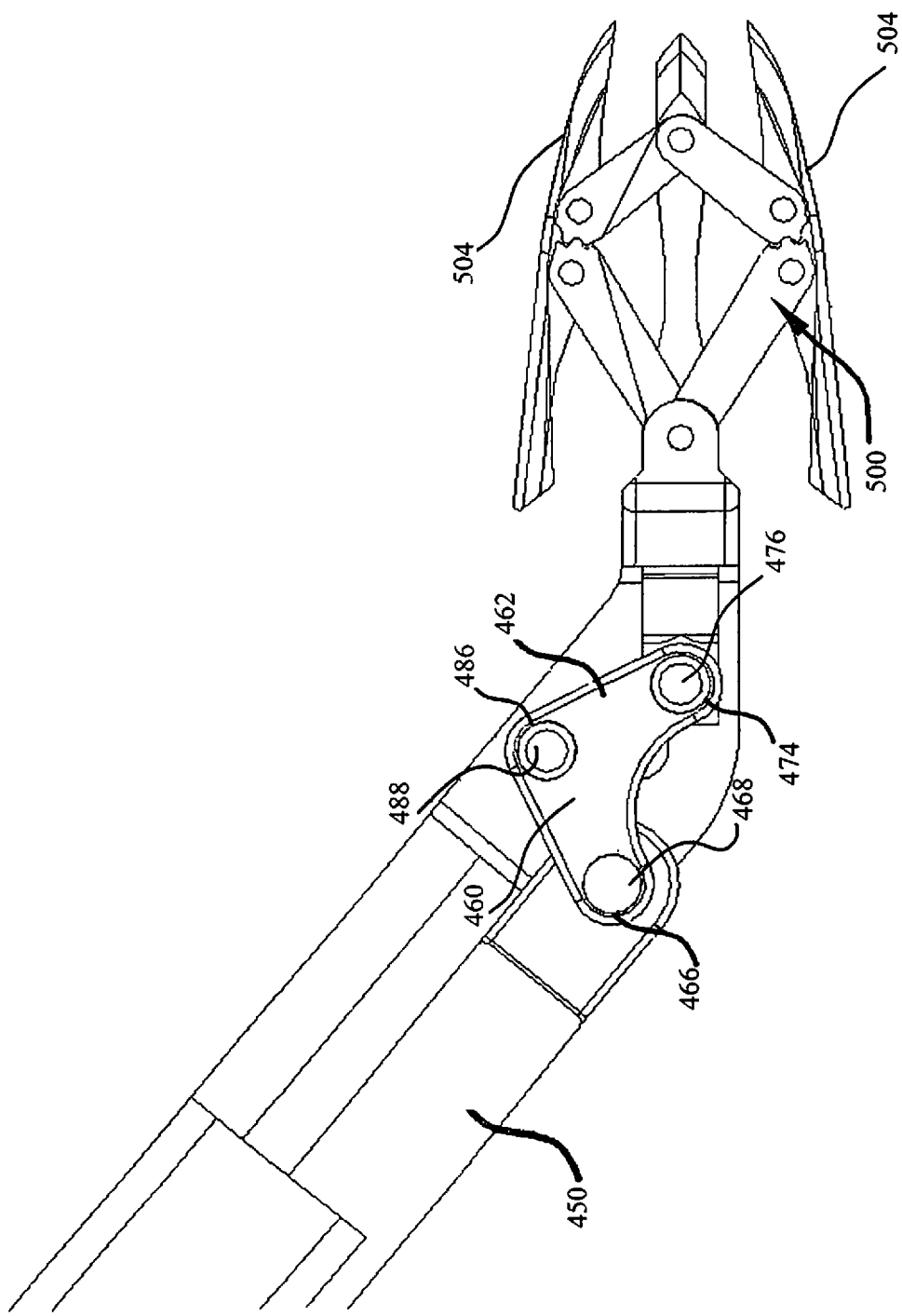
FIG. 18 is a cross section view of the components shown in FIG. 14.
Figure 19:
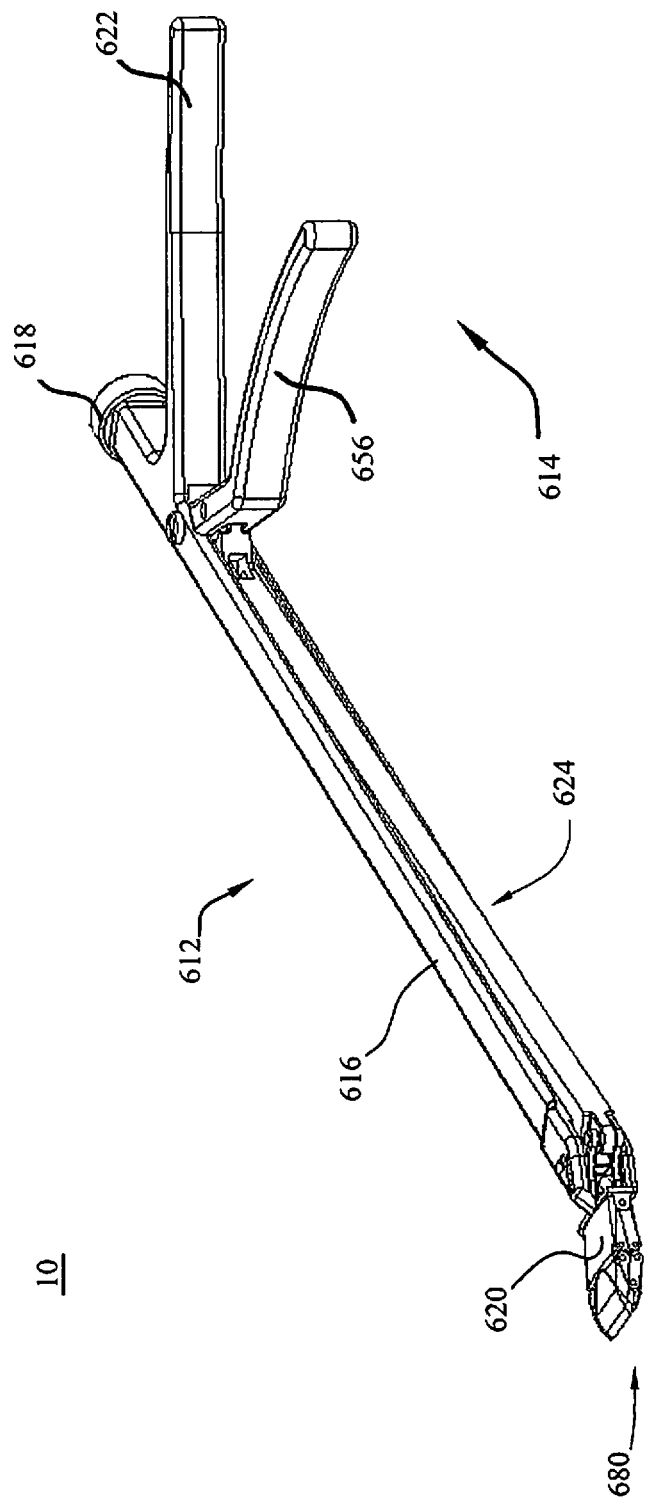
FIG. 19 is a perspective view of components of one embodiment of a surgical system in accordance with the principles of the present disclosure.

Actuator 424 includes a shaft 450, similar to shaft 50 described herein, which extends along axis L1A. Shaft 450 includes a lever 456 configured for movement relative to lever 422 for translating bell crank 434 and/or actuating spacer 480. Bell crank 434 includes a part 460 and a part 462 disposed in substantially perpendicular orientation. Part 460 defines an opening 466, as shown in FIG. 18, configured to receive pin 468. Part 460 is configured for connection with shaft 450 via pin 468. Part 462 defines an opening 474 configured to receive pin 476. Part 462 is configured for connection with spacer 480 via pin 476. Parts 460, 462 define an opening 486 configured to receive pin 488. Translation of pin 488 along slots 438a, 438b and pin 476 along slots 438c, 438d cause parts 460, 462 to rotate to move spacer 480 between a first orientation and a second orientation, as described herein.

Figure 17:
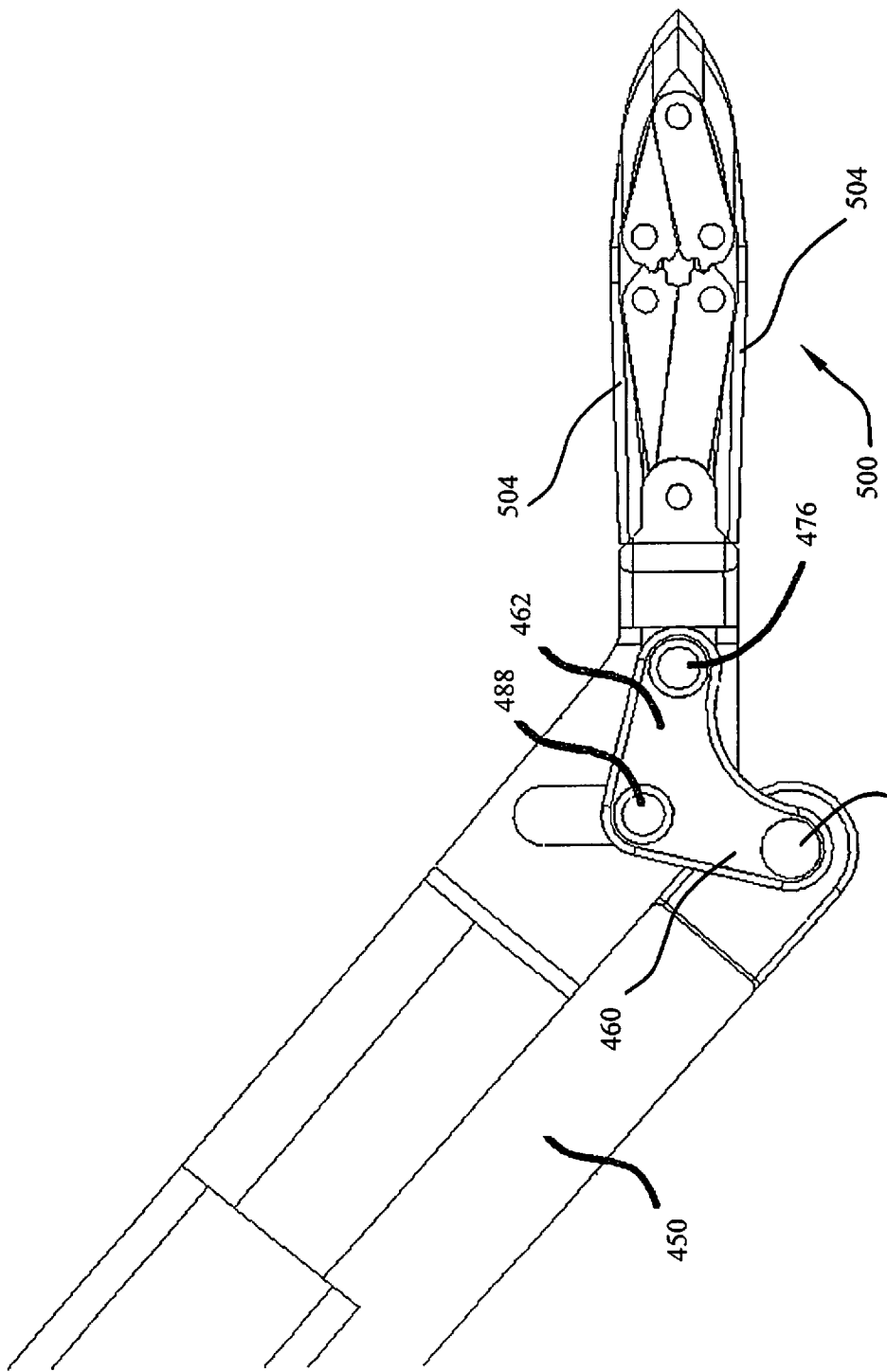
FIG. 17 is a cross section view of the components shown in FIG. 14.

Spacer 480, as shown in FIGS. 17 and 18, includes a linkage 500 positioned between plates 504, similar to the embodiments of linkage and plates described herein. Spacer 480 is adjustable, similar to the embodiments described herein, between a first, collapsed orientation, as shown in FIGS. 15 and 17, and a second, expanded orientation, as shown in FIGS. 16 and 18.

In assembly, operation and use, system 10 including surgical instrument 412, similar to the systems and methods described herein, is employed with a surgical procedure, such as, for example, a fusion treatment of a spine of a patient including vertebrae, an intervertebral disc space and body areas adjacent thereto, as discussed herein. In one embodiment, surgical instrument 412 is delivered through a surgical pathway to a surgical site along a surgical approach into an intervertebral disc space, similar to the surgical procedure and method embodiments described herein.

Figure 20:
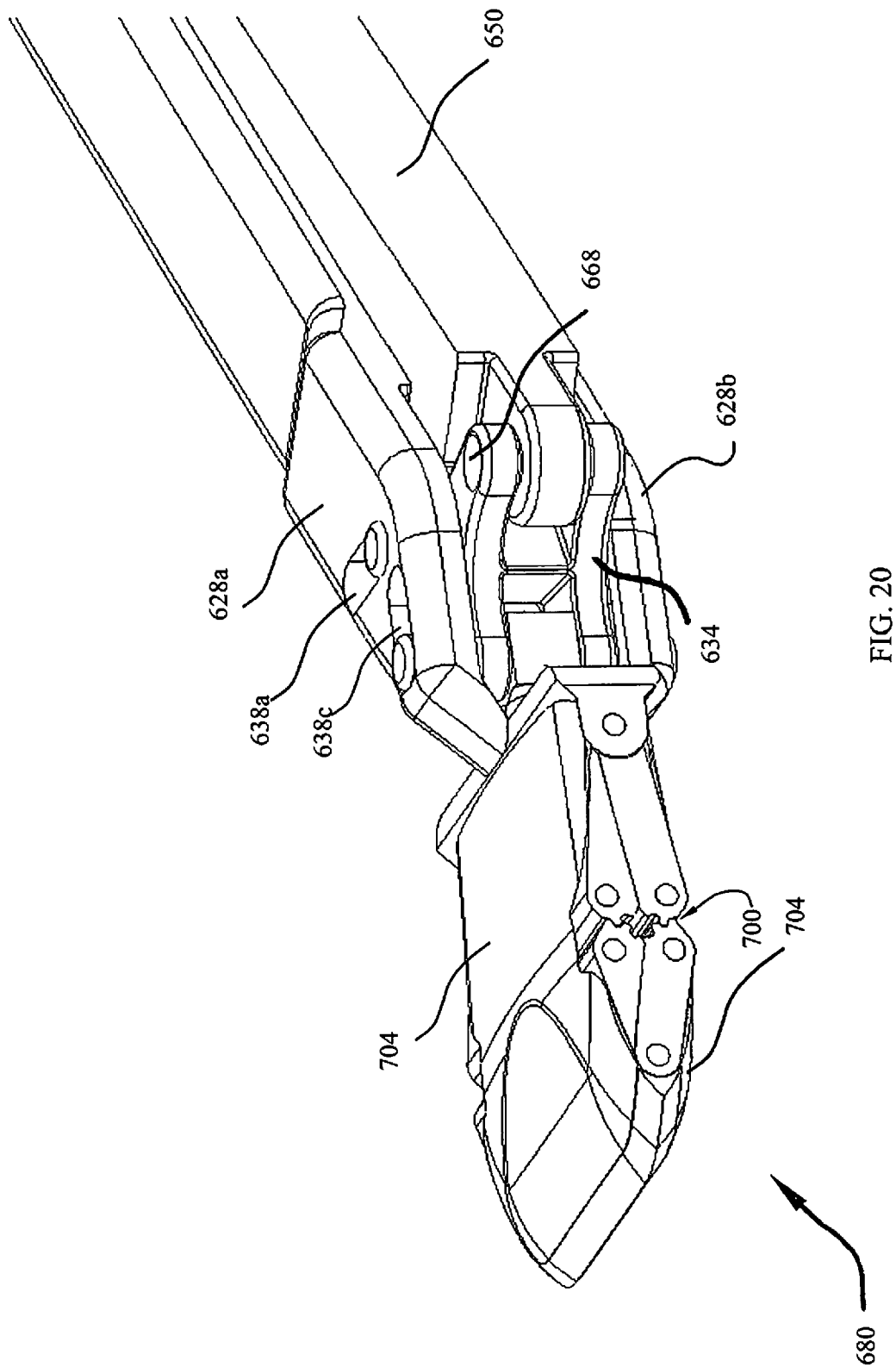
FIG. 20 is a break away view of the components shown in FIG. 19.
Figure 21:
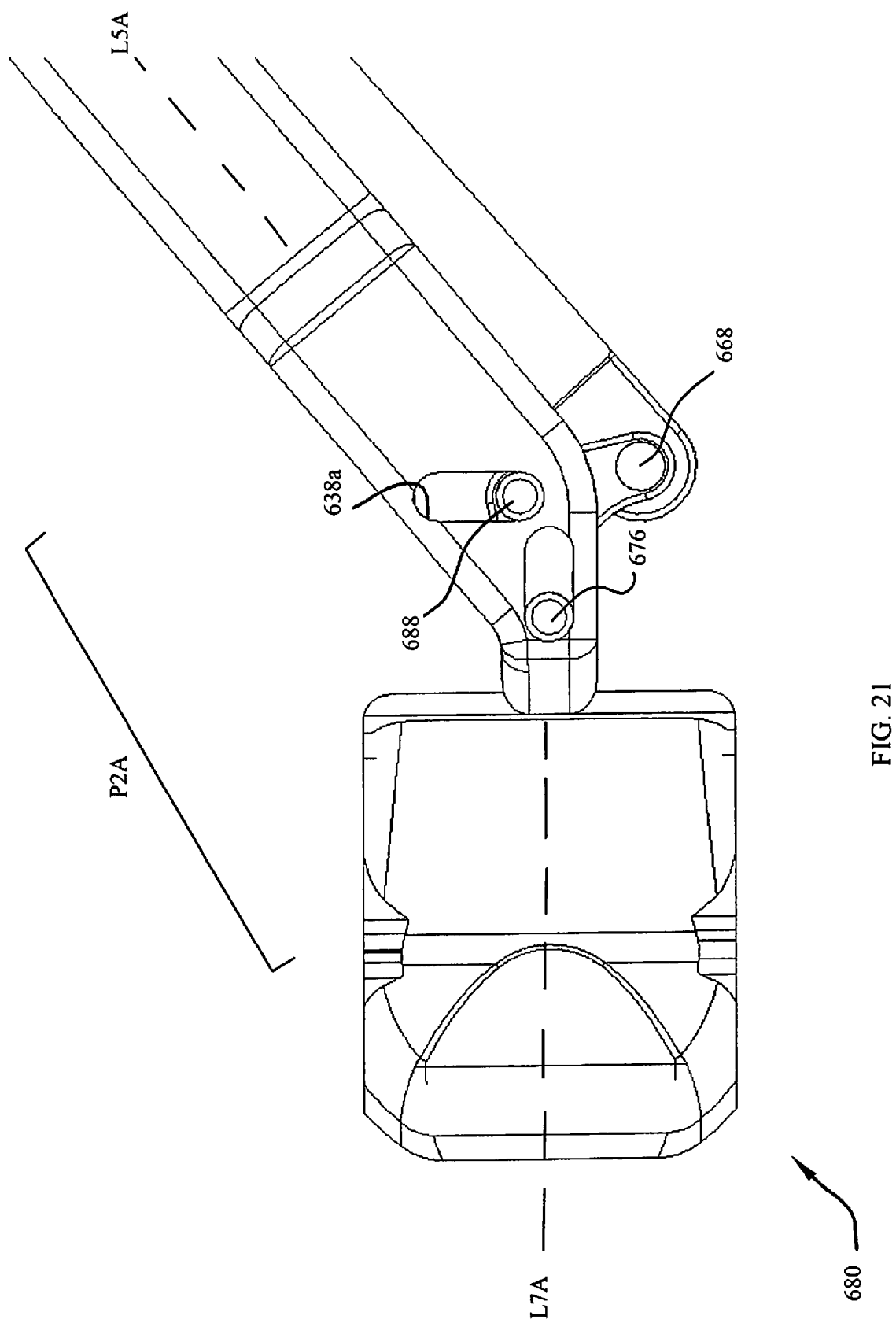
FIG. 21 is a break away view of the components shown in FIG. 19.

In one embodiment, as shown in FIGS. 19-23, system 10, similar to the systems and methods described with regard to FIGS. 1-8, comprises instrument 612, similar to the instruments described herein. Instrument 612 includes a handle 614. Handle 614 includes a shaft 616 extending between an end 618 and an end 620. Shaft 616 defines a longitudinal axis L5A extending in a plane P2A of instrument 612, as shown in FIG. 21.

End 618 includes an actuator, such as, for example, a lever 622, similar to lever 222 described herein. Lever 622 is configured for engagement with a lever of a second member, such as, for example, an actuator 624, similar to actuator 224, as described herein. End 620 includes extensions 620a and 620b that connect with a vertebral spacer 680, similar to spacer 280 described herein.

End 620 includes arms 628a and 628b as shown in FIGS. 20-23, configured for engagement with a bell crank 634, similar to bell crank 234 described herein. Arm 628a includes an inner surface that defines a transverse slot 638a, similar to the slots described herein. Slot 638a is configured for moveable disposal of a pin 688 of bell crank 634 such that bell crank 634 translates along slot 638a between ends thereof. Arm 628b includes an inner surface that defines a slot 638b, similar to the slots described herein. Slot 638b is configured for moveable disposal of pin 688 such that bell crank 634 translates along slot 638b between ends thereof.

The inner surface of arm 628a also defines a transverse slot 638c, similar to the slots described herein. Slot 638c is configured for moveable disposal of a pin 676 of bell crank 634 such that bell crank 634 translates along slot 638c between ends thereof. The inner surface of arm 628b also defines a slot 638d, similar to the slots described herein. Slot 638d is configured for moveable disposal of pin 676 such that bell crank 634 translates along slot 638d between ends thereof.

Actuator 624 includes a shaft 650, similar to shaft 250 described herein, which extends along axis L5A. Shaft 650 includes a lever 656 configured for movement relative to lever 622 for translating bell crank 634 and/or actuating spacer 680. Bell crank 634 is configured for connection with shaft 650 via pin 668 and connection with spacer 680 via pin 676. Translation of pin 688 along slots 638a, 638b and pin 676 along slots 638c, 638d cause bell crank 634 to rotate to move spacer 680 between a first orientation and a second orientation, as described herein.

Spacer 680 defines a longitudinal axis L7A. Axis L7A is disposed at an angular orientation relative to axis L5A. In some embodiments, axis L7A is disposed at an angle relative to axis L5A in a range of approximately 10-160 degrees. In some embodiments, axis L7A may extend transverse and/or at other angular orientations such as acute or obtuse, co-axial and/or may be offset or staggered relative to axis L5A.

Figure 22:
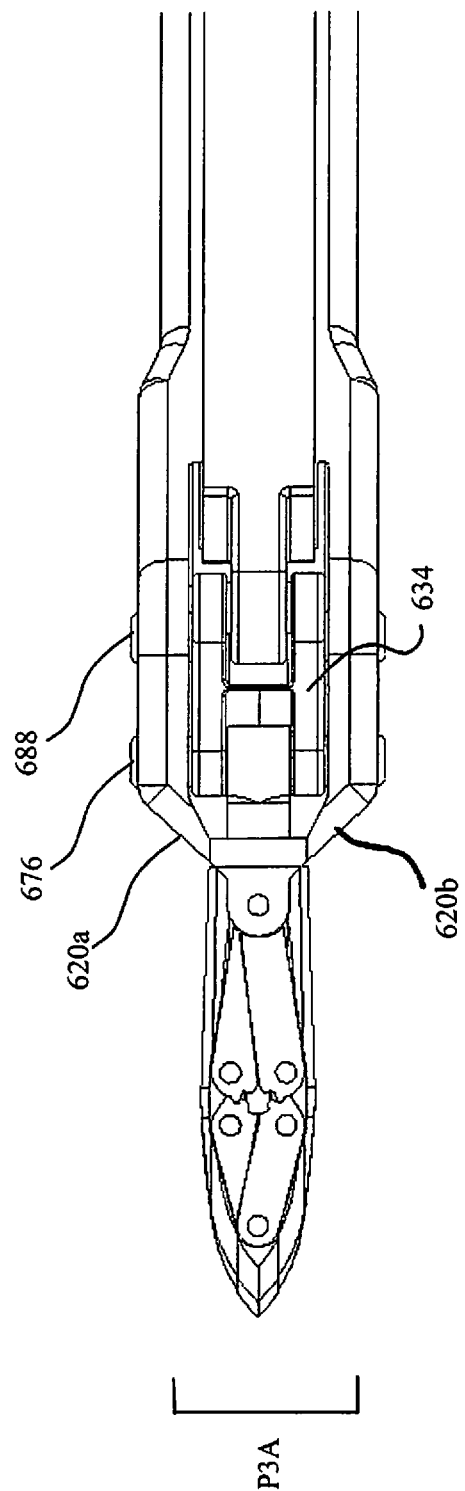
FIG. 22 is a side cross section view of the components shown in FIG. 21.
Figure 23:
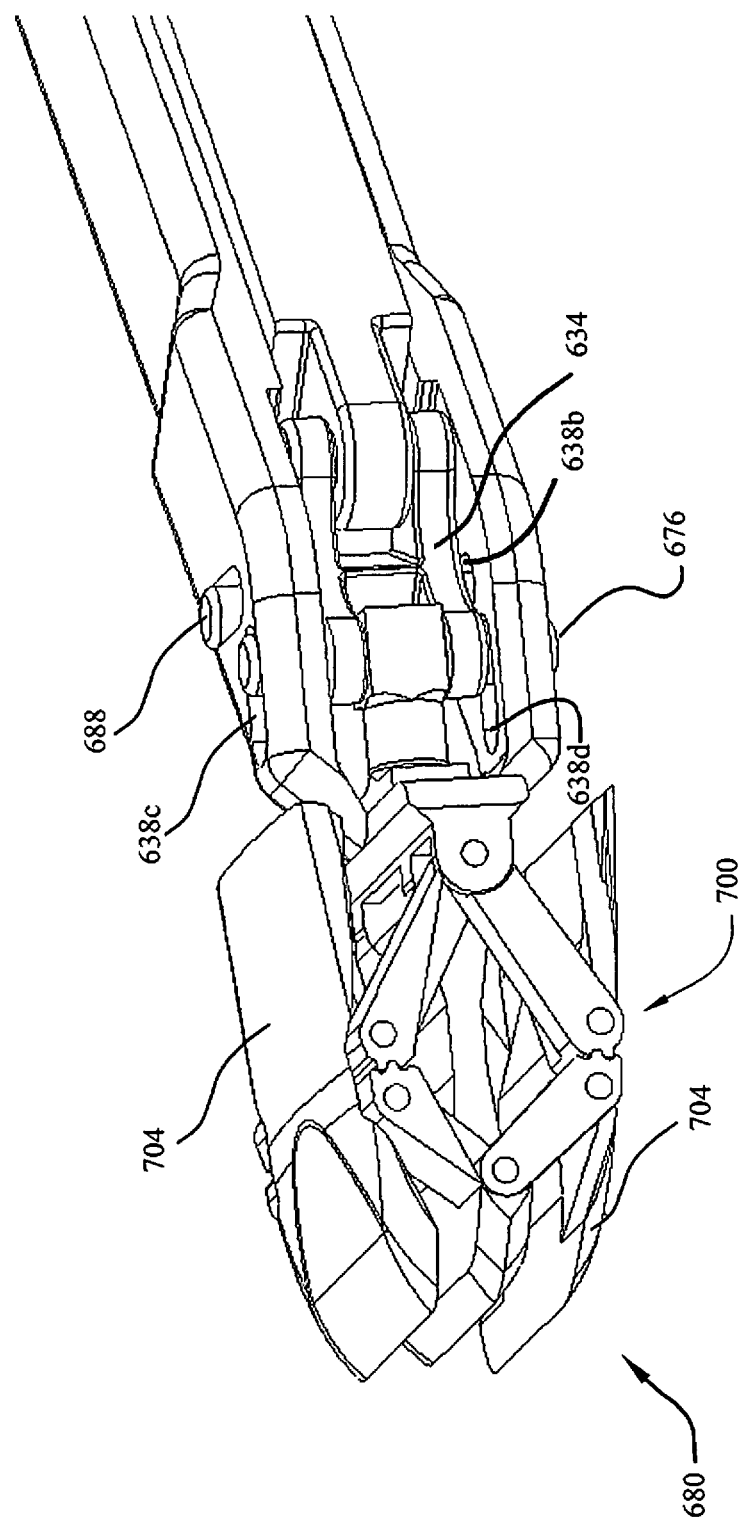
FIG. 23 is a perspective view of the components shown in FIG. 20.

Spacer 680, as shown in FIGS. 20 and 23, includes a linkage 700 positioned between plates 704, similar to the embodiments of linkage and plates described herein. Spacer 680 is adjustable, similar to the embodiments described herein, between a first, collapsed orientation, as shown in FIGS. 20 and 22, and a second, expanded orientation, as shown in FIG. 23.

Plates 704 are positioned on a first side and a second side of spacer 680 to contact vertebral members, such as, for example, endplates of vertebrae, as described herein. Plates 704 each include a contact surface having a surface area to distribute the disc space load created by spacer 680 across a region of the vertebral members. Plates 704 are configured for expansion in a plane P3A of instrument 612, as shown in FIG. 22. Plane P3A is disposed transverse to plane P2A. In some embodiments, plane P2A is disposed substantially orthogonal to plane P3A. In some embodiments, plane P3A comprises an axial plane of vertebrae such that spacer 680 is expandable in the axial plane.

In assembly, operation and use, system 10 including surgical instrument 612, similar to the systems and methods described herein, is employed with a surgical procedure, such as, for example, a fusion treatment of a spine of a patient including vertebrae, an intervertebral disc space and body areas adjacent thereto, as discussed herein. In one embodiment, surgical instrument 612 is delivered through a surgical pathway to a surgical site along a surgical approach into an intervertebral disc space. In one embodiment, surgical instrument 612 is delivered along a lateral surgical approach with access to the intervertebral disc space such that selected anatomical structures can be avoided due to the angled orientation of spacer 680. In one embodiment, surgical instrument 612 is delivered along an OLIF surgical approach with access to the intervertebral disc space such that selected anatomical structures can be avoided due to the angled orientation of spacer 680. In some embodiments, surgical instrument 612 can be employed with a procedure such that surgical instrument 612 is angled laterally to gain access to a disc space laterally and avoid the pelvis. In some embodiments, surgical instrument 612 can be employed with an OLIF procedure to avoid an iliac crest in lateral procedures in the lower lumbar spine.

In one embodiment, as shown in FIGS. 24-28, system 10, similar to the systems and methods described with regard to FIGS. 1-8, comprises instrument 812, similar to the instruments and component parts described herein. Instrument 812 includes a handle 814 for manipulating instrument 812 and its components, translating a bell crank 834 and/or actuating a spacer 880, similar to the handles and levers described herein. In some embodiments, handle 814 comprises a plier and lever configuration, as described herein.

Figure 24:
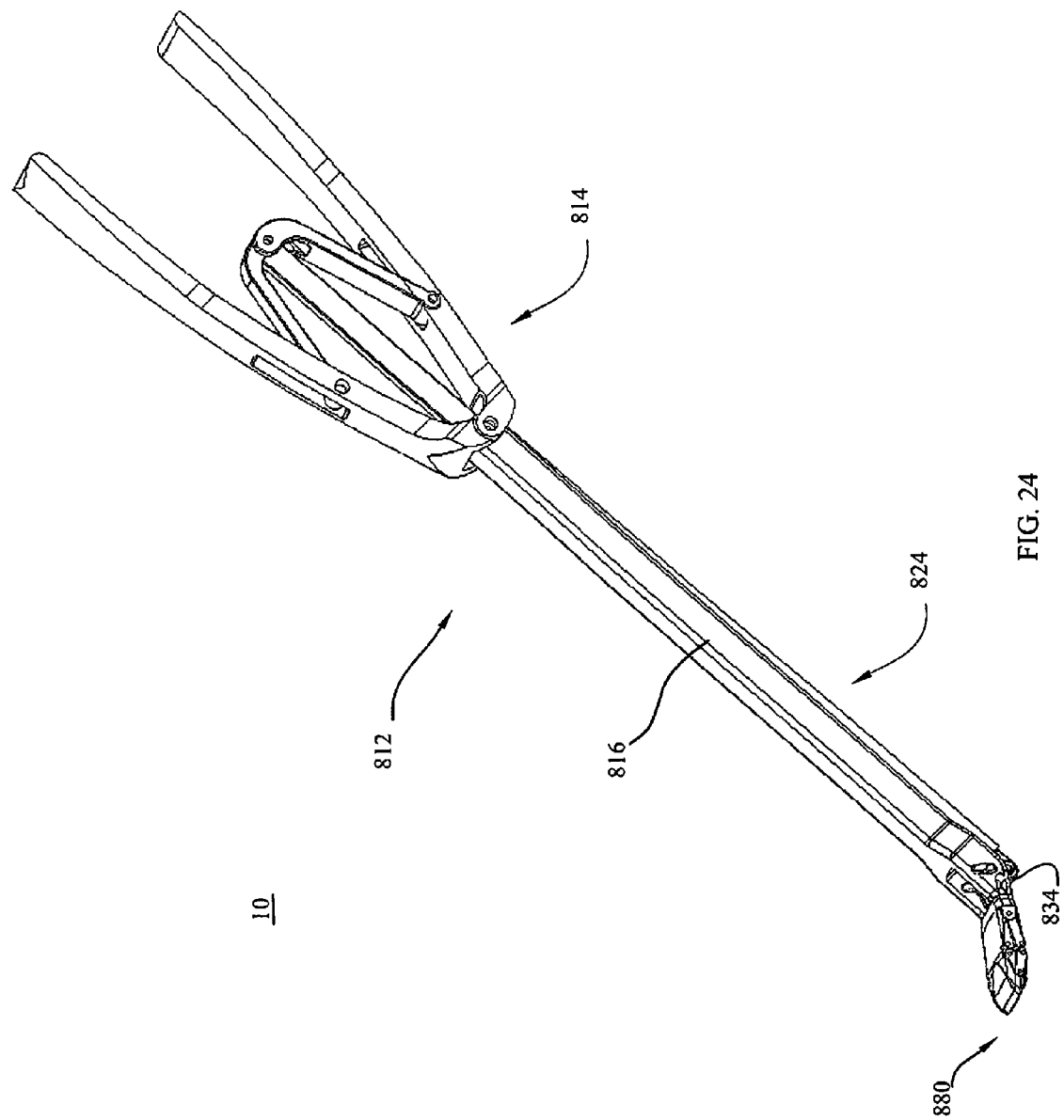
FIG. 24 is a perspective view of components of one embodiment of a surgical system in accordance with the principles of the present disclosure.
Figure 25:
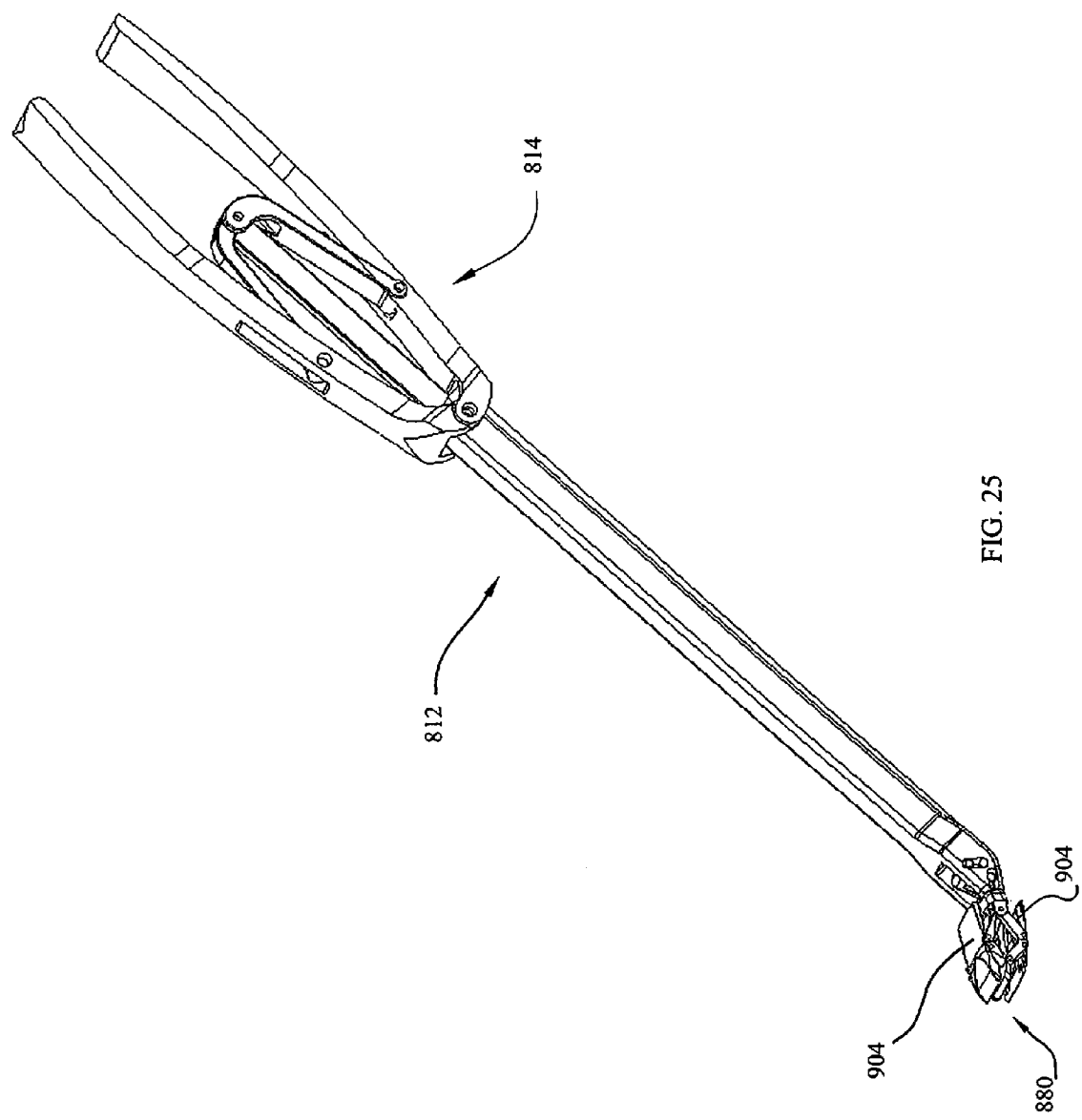
FIG. 25 is a perspective view of the components shown in FIG. 24.

In operation, instrument 812 is manipulated to insert spacer 880 between vertebrae such that spacer 880 is disposed in a collapsed orientation, as shown in FIG. 24, to facilitate introduction, insertion and delivery of spacer 880 along a surgical pathway and/or at a surgical site, similar to that described herein. In the collapsed orientation, spacer 880 is disposed between vertebrae, engaging vertebral tissue and/or having one or both of plates 904 contacting vertebrae.

Figure 26:
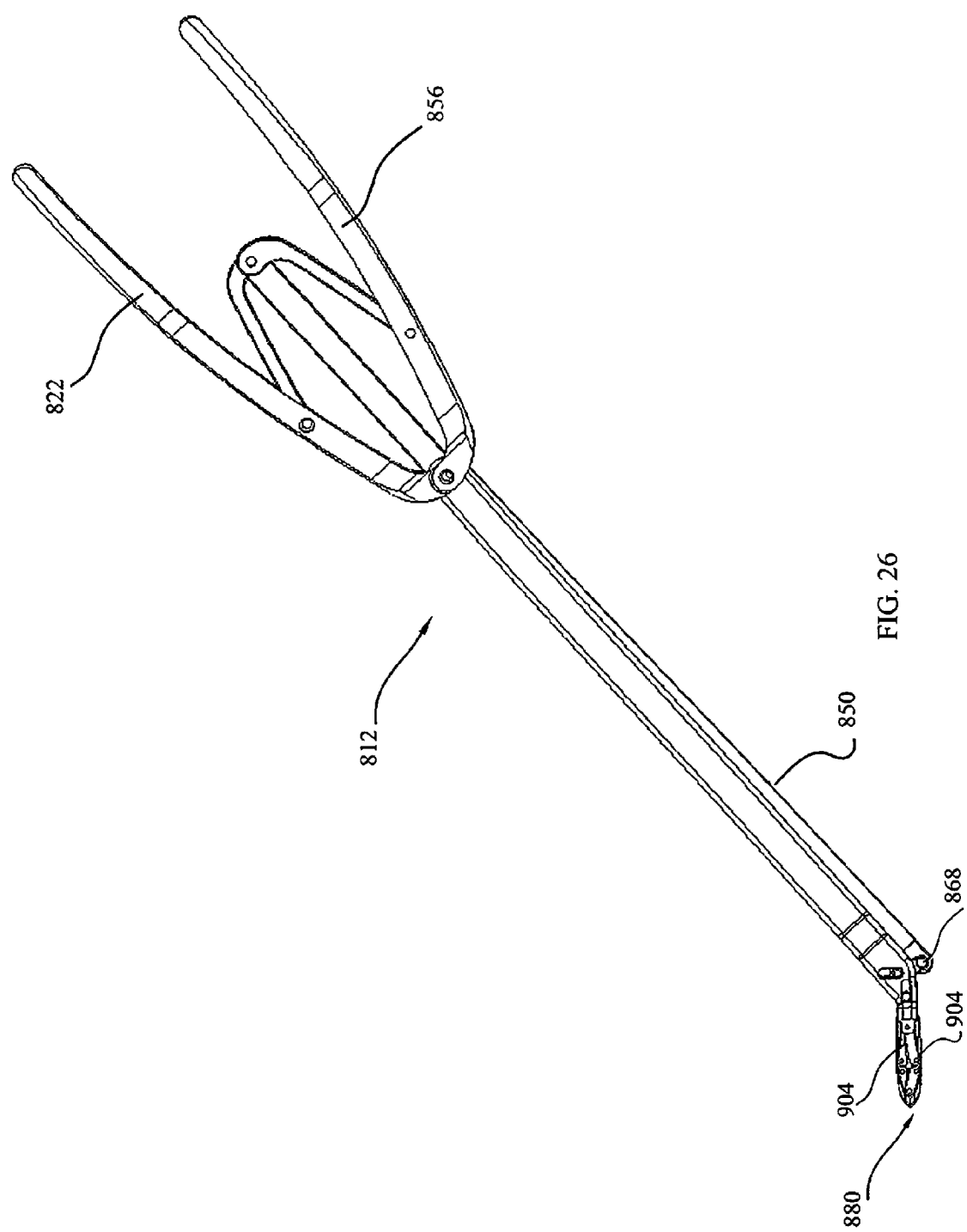
FIG. 26 is a side view of the components shown in FIG. 24.
Figure 27:
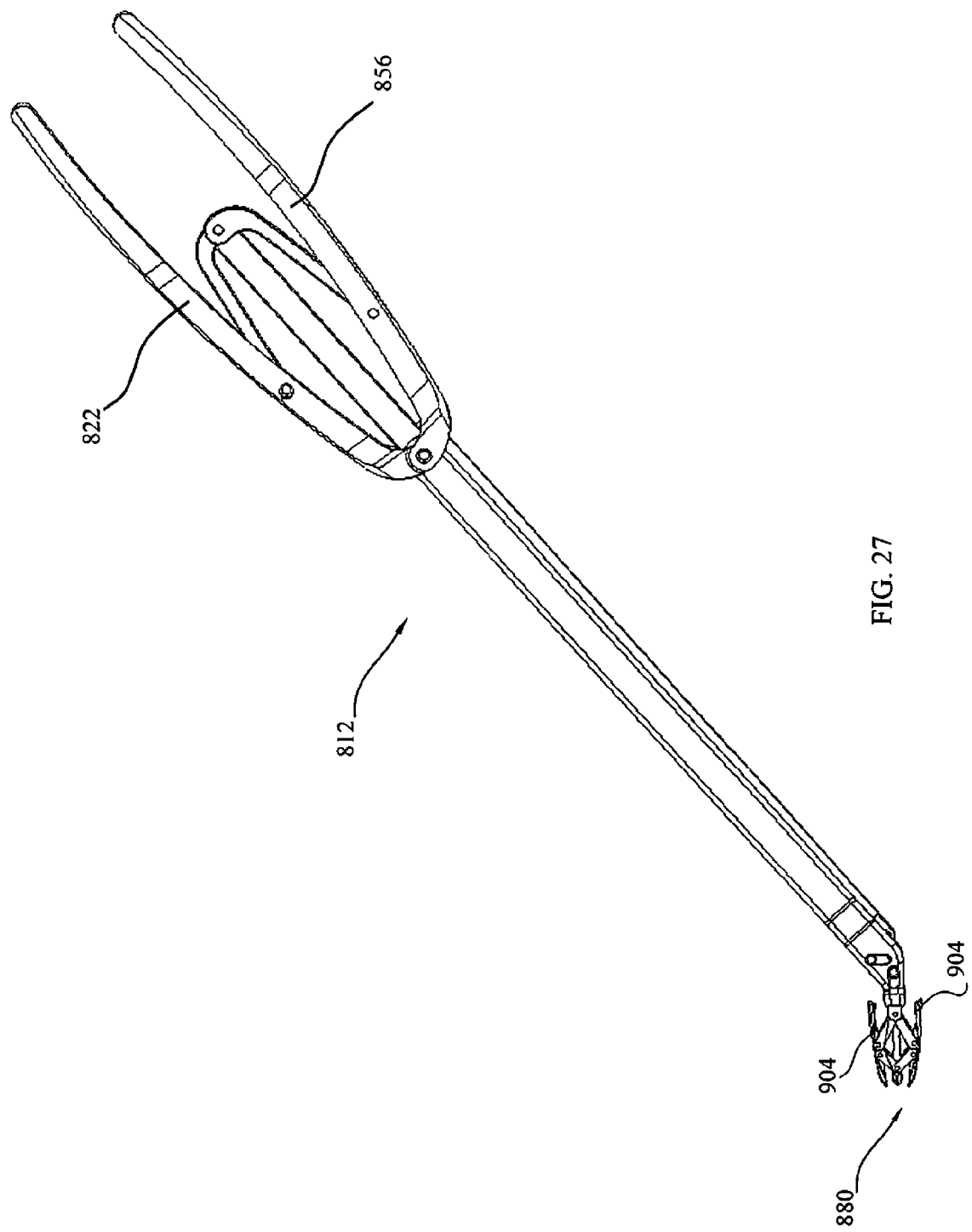
FIG. 27 is a side view of the components shown in FIG. 24.
Figure 28:
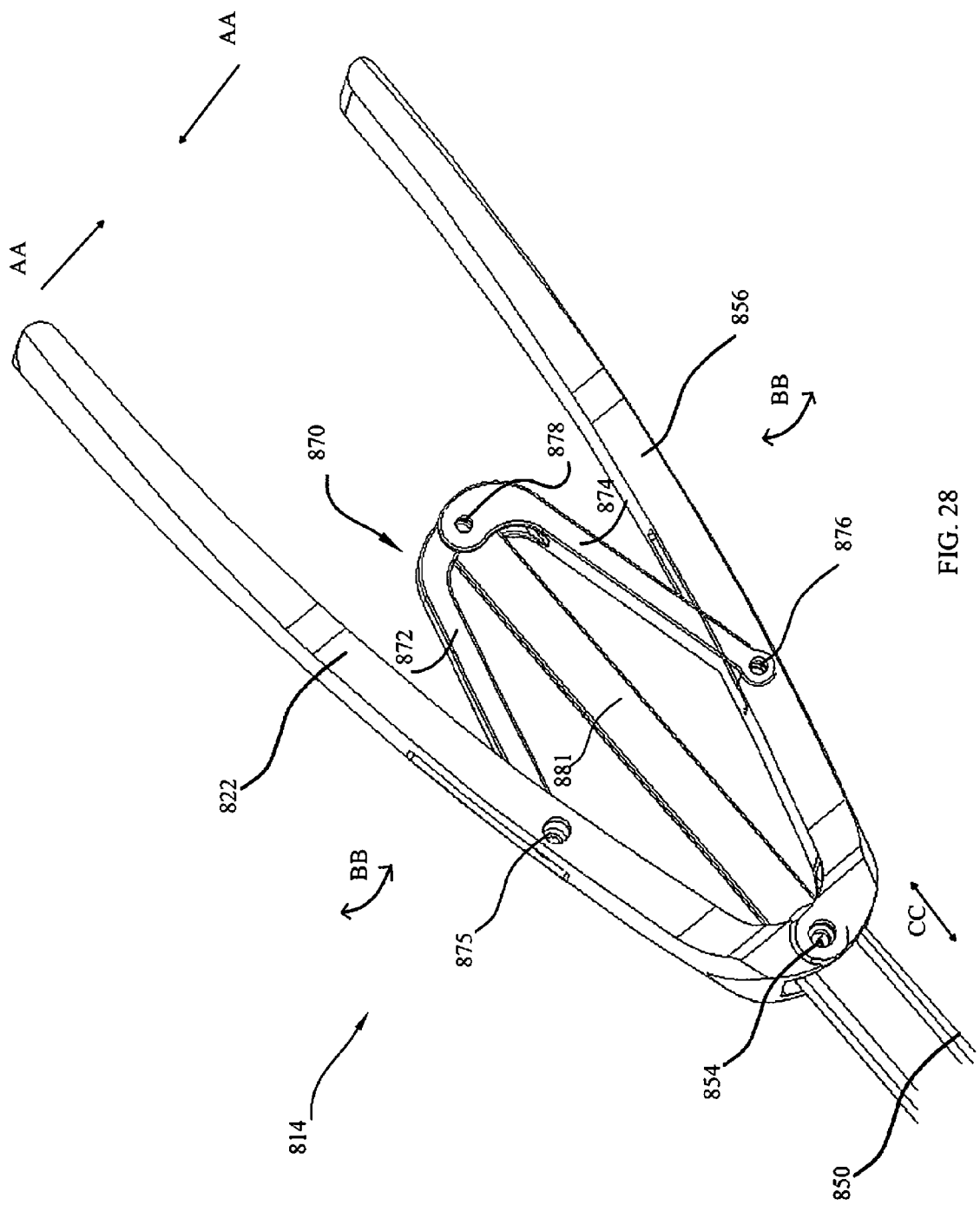
FIG. 28 is a break away view of the components shown in FIG. 24.

For example, in the collapsed orientation, spacer 880 is disposable between vertebrae, engaging vertebral tissue and/or having one or both of plates 904 contacting vertebrae, similar to that described herein. Upon selective disposal of spacer 880 with vertebrae, arms 822, 856 of handle 814 are disposed in a non-compressed orientation, as shown in FIG. 26. Handle 814 is manipulated such that arms 822, 856 are compressed, as shown in FIG. 27, such that arms 822, 856 rotate about a hinge 854, in the directions shown by arrows AA in FIG. 28. Compression of handle 814 causes a linkage 870 to rotate and pivot about pivots 875, 876, 878 such that extensions 872, 874 pivot in opposing directions, as shown by arrows BB. Extensions 872, 874 drive pivot 878 and a link 881 axially to drive a shaft 850 of actuator 824 in translation, in the directions shown by arrows CC. Translation of shaft 850 relative to a shaft 816 actuates spacer 880 between the collapsed and expanded orientations in between vertebrae. As handle 814 is compressed, spacer 880 selectively expands, as shown in FIG. 27, to an enlarged size for contacting, spacing apart and/or spreading vertebrae.

Translation of shaft 850 causes bell crank 834 to pivot about a pin 868, as shown in FIG. 26, relative to shaft 850. One or more pins of bell crank 834 translate along the slots, similar to that described herein, to actuate expansion of spacer 880. Linkages of spacer 880 cause plates 904 to expand and engage vertebral surfaces.

In assembly, operation and use, system 10 including surgical instrument 812, similar to the systems and methods described herein, is employed with a surgical procedure, such as, for example, a fusion treatment of a spine of a patient including vertebrae, an intervertebral disc space and body areas adjacent thereto, as discussed herein. In one embodiment, surgical instrument 812 is delivered through a surgical pathway to a surgical site along a surgical approach into an intervertebral disc space, similar to the surgical procedure and method embodiments described herein.

Figure 29:
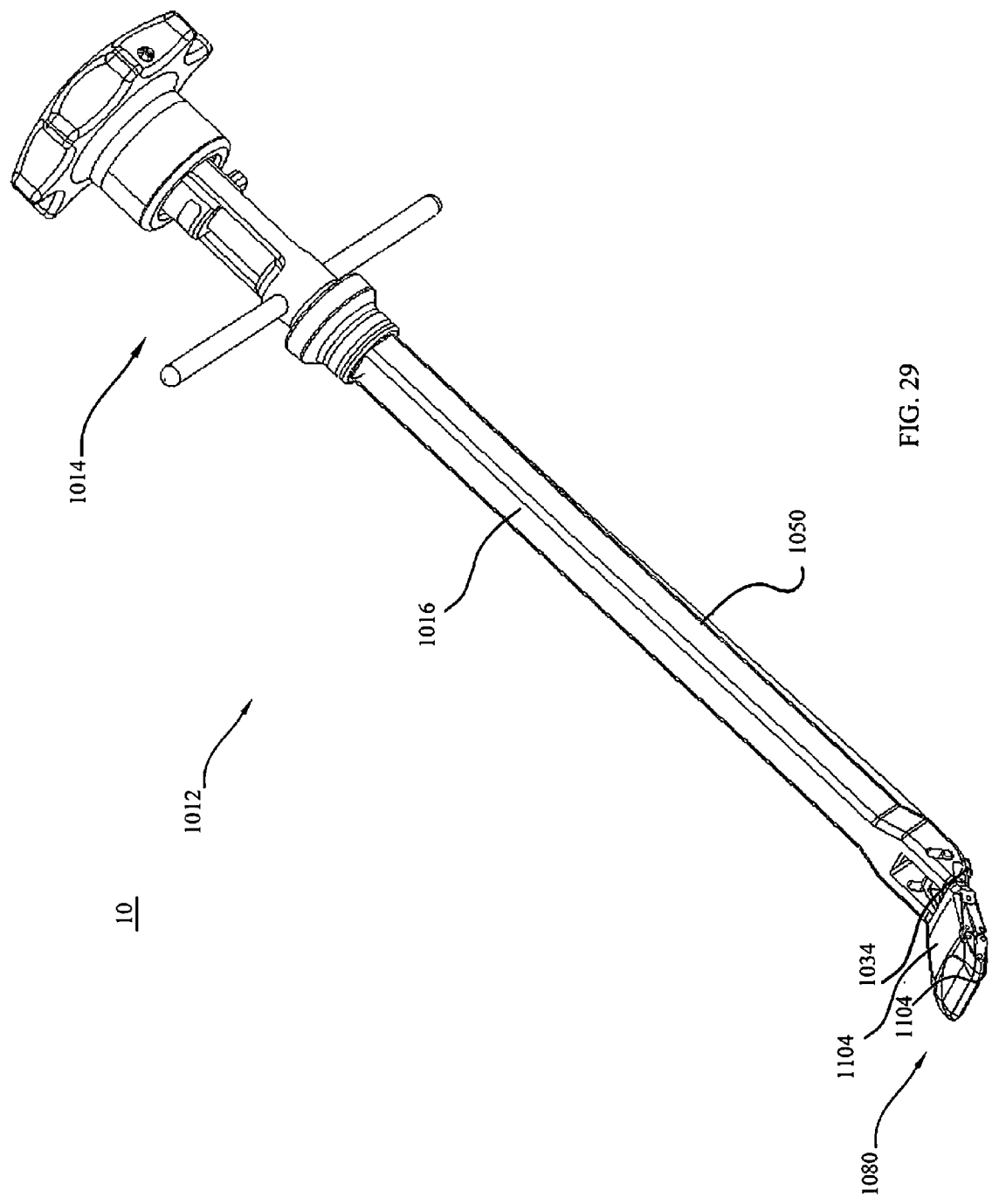
FIG. 29 is a perspective view of components of one embodiment of a surgical system in accordance with the principles of the present disclosure.
Figure 30:
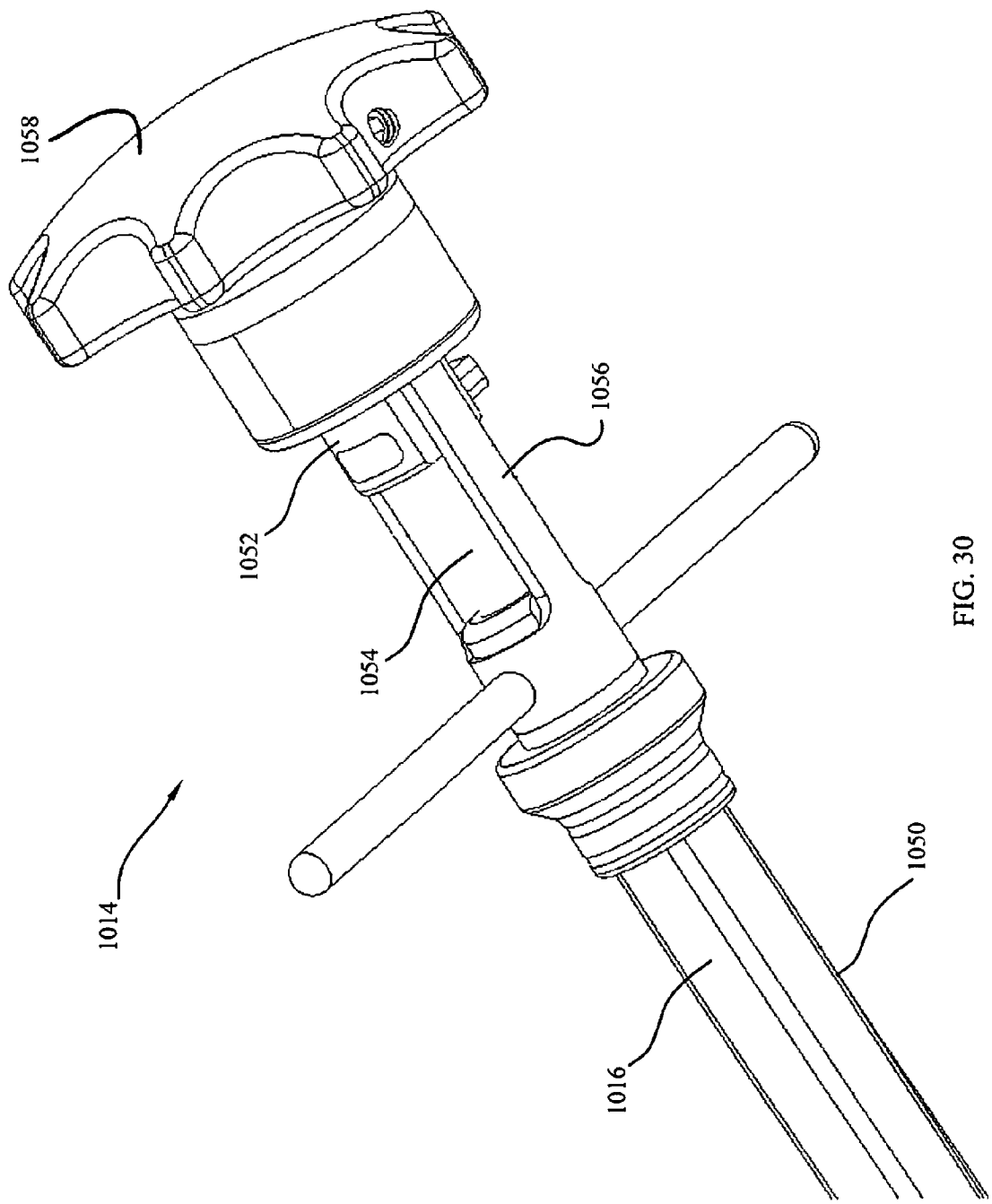
FIG. 30 is a break away view of the components shown in FIG. 29.

In one embodiment, as shown in FIGS. 29 and 30, system 10, similar to the systems and methods described with regard to FIGS. 24-28, comprises instrument 1012, similar to the instruments and component parts described herein. Instrument 1012 includes a handle 1014 for manipulating instrument 1012 and its components, translating a bell crank 1034 and/or actuating a spacer 1080, similar to that described herein. In some embodiments, handle 1014 comprises a threaded rotation/axial translation or screw configuration, as described herein.

Handle 1014 is connected with a shaft 1050, which is connected with bell crank 1034 to actuate expansion and/or contraction of spacer 1080. A screw (not shown) is disposed within a body 1052 of handle 1014 and connected to shaft 1050 via a link 1054 disposed within a frame 1056. An actuator, such as, for example, a knob 1058 rotates and threadably engages the screw to translate the screw axially for engagement with shaft 1050. The screw is engageable with shaft 1050 to translate shaft 1050 axially in both a proximal direction and a distal direction relative to a shaft 1016 to actuate spacer 1080 between a collapsed orientation and an expanded orientation, similar to that described herein. Frame 1056 is connected to shaft 1016.

For example, in a collapsed orientation, spacer 1080 is disposable between vertebrae, engaging vertebral tissue and/or having one or both of plates 1104 contacting vertebrae, similar to that described herein. Knob 1058 is rotated in a clockwise direction to threadably engage the screw to draw the screw and shaft 1050 in a proximal direction relative to shaft 1016. Translation of shaft 1050 causes bell crank 1034 to pivot relative to shaft 1050. One or more pins of bell crank 1034 translate along the slots, similar to that described herein, to actuate expansion of spacer 1080. Linkages of spacer 1080 cause plates 1104 to expand and engage vertebral surface. In some embodiments, knob 1058 is rotatable in a counter-clockwise direction to threadably engage the screw to drive the screw and shaft 1050 in a distal direction relative to shaft 1016 to contract spacer 1080 for disposal in the collapsed orientation.

In assembly, operation and use, system 10 including surgical instrument 1012, similar to the systems and methods described herein, is employed with a surgical procedure, such as, for example, a fusion treatment of a spine of a patient including vertebrae, an intervertebral disc space and body areas adjacent thereto, as discussed herein. In one embodiment, surgical instrument 1012 is delivered through a surgical pathway to a surgical site along a surgical approach into an intervertebral disc space, similar to the surgical procedure and method embodiments described herein.

In various embodiments, sensors (including, but not limited to strain gages, pressure sensors, piezoelectric elements, electromagnetic elements, and RF coils for distance measurement) may be embedded in various components of the system 10 in order to provide real-time feedback and/or measurement capabilities to a surgeon using the system 10. For example, strain gage devices or pressure sensors may be embedded in and/or placed on an exterior surface of opposing plates 104 (see FIG. 4, for example) of the spacer 80 or linkage 100. These sensors may provide an indication of the pressure applied by plates 104 to adjacent tissues as the linkage 100 is engaged by operation of the levers 56, 22. In other embodiments, a known geometrical relationship may be established between the movement of the levers 56, 22 and the plates 104 such that sensors placed in and/or on the levers 22, 56 may be indicative of pressure applied by the plates 104, angulation of the plates 104 relative to one another, and/or relative distance between the plates 104. Placement of sensors in the levers 22, 56 may enable them to be separable from the working end (i.e. the spacer 80) of the system 10 such that the instrument 12 may be effectively sterilized without exposing the sensors in the levers 22, 56 to the extreme conditions of sterilization procedures. As will be appreciated by one of skill in the art, any sensors applied to the instrument 12 may be connected by wireless means (including, but not limited to low-power RFID, RE coupling, Bluetooth®, wifi) to a base unit, tablet and/or other computing device capable of recording pressures, distances and/or angulations experienced by various components of the instrument 12 during a surgical procedure.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a first member defining a longitudinal axis;
   a second member being connected with a pivot; and
   a third member defining a first axis disposed at an angular orientation relative to the longitudinal axis and being connected with the pivot,
   wherein the second member is translatable relative to the first member to rotate the pivot to move the third member between a first orientation and a second orientation to space vertebral tissue,
   wherein the third member includes a shaft connected with the pivot, and
   wherein rotation of the pivot translates the shaft to move the third member between a first orientation and a second orientation to space vertebral tissue.

2. A surgical instrument as recited in claim 1, wherein the pivot comprises a crank.

3. A surgical instrument as recited in claim 1, wherein the pivot comprises a first hinge connected with the second member and a second hinge connected with the third member.

4. A surgical instrument as recited in claim 1, wherein the pivot comprises a first part connected with the second member and a second part connected with the third member, the parts being disposed in a relative perpendicular orientation.

5. A surgical instrument as recited in claim 4, wherein the first part comprises a first hinge connected with the second member and the second part comprises a second hinge connected with the third member.

6. A surgical instrument as recited in claim 1, wherein the first member includes a surface that defines a cavity such that the pivot is movable therein.

7. A surgical instrument as recited in claim wherein the first member includes a surface that defines an elongated slot such that the pivot is translatable therein.

8. A surgical instrument as recited in claim 7, wherein the pivot includes an element that is translatable within the slot in a transverse orientation relative to the longitudinal axis.

9. A surgical instrument as recited in claim 1, wherein the shaft is connected with an expandable linkage and opposing plates that engage the vertebral tissue.

10. A surgical instrument as recited in claim 1, wherein the third member includes an expandable linkage.

11. A surgical instrument as recited in claim 1, wherein the third member includes a linkage including a plurality of links having non-equal lengths in a configuration to provide adjustable spacing.

12. A surgical instrument as recited in claim 1, wherein the first member includes a first lever and the second member includes a second lever that are engageable to translate the second member relative to the first member.

13. A surgical instrument as recited in claim 1 wherein the third member is configured to space vertebral tissue laterally relative to an alignment of the first member and the second member.

14. A vertebral distractor comprising:
- a handle including a shaft defining a longitudinal axis;
- an actuator;
- a vertebral spacer defining a first axis disposed at an angular orientation relative to the longitudinal axis and a linkage shaft; and
- a bell crank that comprises a hinge connected with the actuator and a hinge connected with the linkage shaft,
- wherein the actuator is translatable relative to the shaft of the handle to rotate the bell crank to translate the linkage shaft to expand the vertebral spacer.

15. A surgical instrument comprising:
- a first member defining a longitudinal axis;
- a second member being connected with a pivot; and
- a third member defining a first axis disposed at an angular orientation relative to the longitudinal axis and being connected with the pivot,
- wherein the second member is translatable relative to the first member to rotate the pivot to move the third member between a first orientation and a second orientation to space vertebral tissue,
- wherein the third member includes a shaft connected with an expandable linkage and opposing plates that engage the vertebral tissue.

16. A surgical instrument as recited in claim 15, wherein the pivot comprises a crank.

17. A surgical instrument as recited in claim 15, wherein the pivot comprises a first hinge connected with the second member and a second hinge connected with the third member.

18. A surgical instrument as recited in claim 15, wherein the pivot comprises a first part connected with the second member and a second part connected with the third member, the parts being disposed in a relative perpendicular orientation.

19. A surgical instrument as recited in claim 18, wherein the first part comprises a first hinge connected with the second member and the second part comprises a second hinge connected with the third member.

20. A surgical instrument as recited in claim 15, wherein the first member includes a surface that defines a cavity such that the pivot is movable therein.

* * * * *

UNITED STATES PATENT AND TRADEMARK OFFICE
CERTIFICATE OF CORRECTION

PATENT NO. : 9,585,650 B2
APPLICATION NO. : 14/290518
DATED : March 7, 2017
INVENTOR(S) : Lim et al.

Page 1 of 2

It is certified that error appears in the above-identified patent and that said Letters Patent is hereby corrected as shown below:

In the Drawings

Fig. 5, Drawing Sheet 3 of 25, delete " 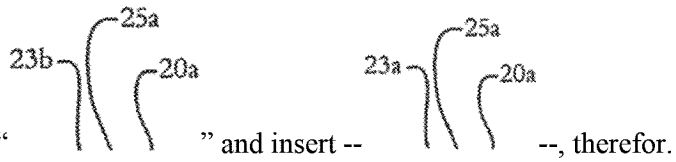 " and insert -- --, therefor.

Fig. 10, Drawing Sheet 6 of 25, delete " 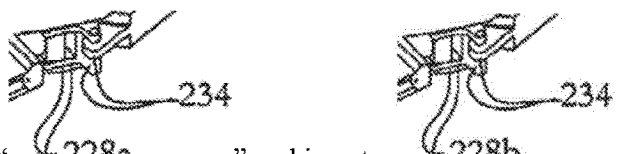 " and insert -- --, therefor.

In the Specification

Column 4, Line 21, delete "modus" and insert -- models --, therefor.

Column 5, Line 43, delete "polyimide, polyimide," and insert -- polyamide, polyimide, --, therefor.

Column 5, Line 45, delete "example;" and insert -- example, --, therefor.

Column 9, Line 54, delete "V2" and insert -- V2. --, therefor.

Column 10, Line 33, delete "End 250" and insert -- End 252 --, therefor.

Column 10, Line 63, delete "pin," and insert -- pin --, therefor.

Column 12, Line 62, delete "628b" and insert -- 628b, --, therefor.

Signed and Sealed this
Twenty-fourth Day of July, 2018

Andrei Iancu
*Director of the United States Patent and Trademark Office*

CERTIFICATE OF CORRECTION (continued)
U.S. Pat. No. 9,585,650 B2

Column 15, Line 28, delete "surface." and insert -- surfaces. --, therefor.

Column 16, Line 2, delete "RFID, RE" and insert -- RFID, RF --, therefor.

In the Claims

Column 16, Line 49, Claim 7, delete "claim" and insert -- claim 1, --, therefor.

Column 17, Line 1, Claim 13, delete "claim 1" and insert -- claim 1, --, therefor.